US009504761B2

(12) United States Patent
Santra et al.

(10) Patent No.: US 9,504,761 B2
(45) Date of Patent: Nov. 29, 2016

(54) STABILIZED CHITOSAN-BASED NANOPARTICLES AND METHODS FOR MAKING THE SAME

(75) Inventors: Swadeshmukul Santra, Orlando, FL (US); James Turkson, Orlando, FL (US); Astha Malhotra, Orlando, FL (US); Padmavathy Tallury, Chennai (IN)

(73) Assignee: University of Central Florida Research Foundation, Inc., Orlando, FL (US)

( * ) Notice: Subject to any disclaimer, the term of this patent is extended or adjusted under 35 U.S.C. 154(b) by 0 days.

(21) Appl. No.: 13/090,732

(22) Filed: Apr. 20, 2011

(65) Prior Publication Data
US 2012/0269729 A1 Oct. 25, 2012

(51) Int. Cl.
*A61K 47/48* (2006.01)
*C08B 37/00* (2006.01)
*C08L 5/08* (2006.01)
*C08L 77/00* (2006.01)
*C08J 3/16* (2006.01)
*C08B 37/08* (2006.01)

(52) U.S. Cl.
CPC ... *A61K 47/48923* (2013.01); *A61K 47/48107* (2013.01); *A61K 47/48907* (2013.01); *C08B 37/003* (2013.01); *C08J 3/16* (2013.01); *C08L 5/08* (2013.01); *C08J 2305/08* (2013.01)

(58) Field of Classification Search
None
See application file for complete search history.

(56) References Cited

U.S. PATENT DOCUMENTS

| 5,693,751 | A | 12/1997 | Sakurai et al. | |
|---|---|---|---|---|
| 7,541,028 | B2 * | 6/2009 | Sung et al. | 424/130.1 |
| 2005/0226938 | A1 | 10/2005 | Borbely et al. | |
| 2009/0004118 | A1 * | 1/2009 | Nie et al. | 424/9.35 |

OTHER PUBLICATIONS

Liu, Z., et al., "Polysaccharides-based nanoparticles as drug delivery systems", 2008, Adv. Drug, Del. Rev., 60, pp. 1650-1662.*
De, T.K. et al., "Solution behaviour of Aerosol OT in non-polar solvents", Advances in Colloid and Interface Science, 1995, vol. 59, pp. 95-193.
Dechantsreiter, M.A., et al., "N-Methylated Cyclic RGD Peptides as Highly Active and Selective αvβ3 Integrin Antagonists", Journal of Medicinal Chemistry, 1999, vol. 42(16), pp. 3033-3040.
Santra, S., et al., "Conjugation of Biomolecules with Luminophore-Doped Silica Nanoparticles for Photostable Biomarkers", Analytical Chemistry, 2001, vol. 73(20), pp. 4988-4993.
Perkins, A.C. et al., "Radionuclide imaging in drug development", Current Pharmaceutical Design, 2004, vol. 10(24), pp. 2907-2921.
Longjiang Zhang et al., "Delivery of therapeutic radioisotopes using nanoparticle platforms: potential benefit in systemic radiation therapy", Nanotechnology, Science and Applications, 2010, vol. 2010:3, pp. 159-170.
So, M.-K. et al., "Self-Illuminating Quantum Dot Conjugates for In Vivo Imaging", J. Nat. Biotechnol., Mar. 2006, vol. 24, pp. 339-343.
Gupta, Ram B et al. "Nanoparticle technology for Drug Deliver", Taylor & Francis, 2006, Chapters 1, 4, 5 and 6, pp. 1-19 and 85-160.
Li, Linlin et al., "Magnetic and fluorescent multifunctional chitosan nanoparticles as smart delivery system", IOP publishing: Nanotechnology, 2007, vol. 18, article 405102, pp. 1-6.
Wang, Yujun et al., "In situ preparation of magnetic chitosan/Fe3O4 composite nanoparticles in tiny pools of water-in-oil microemulsion", Elsevier, Reactive & Functional Polymers, 2006, vol. 66, pp. 1557-1558.
Wang, Yujun et al., "Adsorpotion of bovin serum albumin (BSA) onto the magnetic chitosan nanoparticles prepared by a micremulsion system", Bioresource Technology, 2008, vol. 99, pp. 3881-3384.
Shikata, Futoshi et al., "In vitro cellular accumulation of gadolinium incorporated into chitosan nanoparticles designed for neutron-capture therapy of cancer", Europan Journal of Pharmaceutics and Biopharmaceutics, 2002, vol. 53, pp. 57-63.
Shamra, Parvesh et al., "Nanoparticles for bioimaging", Advances in Colloid and Interface Science, 2006, vol. 123-126, pp. 471-485.
Santra, Swadeshmukul et al, "Synthesis and Characterization of Fluorescent, Radio-Opaque, and Paramagentic Silica Nanoparticles for Multimodal Bioimaging Applications", Advance Materials, 2005, vol. 17, pp. 2165-2169.
Mansouri, Sania et al., Characterization of folate-chitosan-DNA nanoparticles for gene therapy, Biomaterials, 2006, vol. 27, pp. 2060-2065.
Zhi, J et al., "Adsorption of diuretic furosemide onto chitosan nanoparticles prepared with a water-in-oil nanoemulsion system", Reactive and Functional Polymers, 2005, vol. 65, pp. 249-257.
Rekha, M.R. et al., "pH Sensitive Succinyl Chitosan Microparticles: A Preliminary Investigation Towards Oral Insulin Deliver, Trends in Biomaterials and Artificial Organs", 2008, vol. 21, pp. 107-115.
Banerjee, S., "A simple strategy for quantum dot assisted selective detection of cadmium ions", 2008, Chemical Communications, vol. 25, 3037-3039.
Felt, Olivia et al., "Chitosan: A Unique Polysaccharide for Drug Delivery", Drug Development and Industrial Pharmacy, 1998, vol. 24, No. 11, pp. 979-993.
S. S. Davis et al., "Polymers in Drug Delivery", Current Opinion in Colloid & Interface Science, 1996, vol. 1, pp. 660-666.
H. Honarkar et al., "Applications of biopolymers I: chitosan", Monatshefte Fur Chemie, 2009, vol. 140, pp. 1403-1420.
R. Jayakumar et al, "Chitosan conjugated DNA nanoparticles in gene therapy", Carbohydrate Polymers, 2010, vol. 79, pp. 1-8.

(Continued)

*Primary Examiner* — Michael G Hartley
*Assistant Examiner* — Lance Rider
(74) *Attorney, Agent, or Firm* — Timothy H. Van Dyke; Beusse, Wolter, Sanks & Maire, PLLC

(57) ABSTRACT

A stabilized chitosan-based nanoparticle is provided having a chitosan polymer and a hydrophilic dispersing agent. In the stabilized nanoparticle, chains of the chitosan polymer electrostatically interact with chains of the hydrophilic dispersing agent to form an entangled network between the chitosan polymer and the hydrophilic dispersing agent. The stabilized chitosan-based nanoparticle has optimal particle integrity and stability properties under physiological conditions.

9 Claims, 30 Drawing Sheets

(56) References Cited

OTHER PUBLICATIONS

S. A. Agnihotri et al., "Recent advances on chitosan-based micro- and nanoparticles in drug delivery", Journal of Controlled Release, 2004, vol. 100, pp. 5-28.

T. Nam et al., "Tumor Targeting Chitosan Nanoparticles for Dual-Modality Optical/MR Cancer Imaging", Bioconjugate Chemistry, 2010, vol. 21, pp. 578-582.

Q. L. Nie et al., Synthesis and characterization of monodisperse chitosan nanoparticles with embedded quantum dots, Nanotechnology, 2006, vol. 17, pp. 140-144.

M. Sandros et al., "InGaP@ZnS-Enriched Chitosan Nanoparticles: AVersatile Fluorescent Probe for Deep-Tissue Imaging", Advanced Functional Materials, 2007, vol. 17, pp. 3724-3730.

W. K. Wan et al., "Use of degradable and nondegradable nanomaterials for controlled release", Nanomedicine, 2007, vol. 2, pp. 483-509.

K. D. Yao et al., "Microcapsules/microspheres Related to Chitosan", Journal of Macromolecular Science—Reviews in Macromolecular Chemistry and Physics, 1995, C35, pp. 155-180.

V. Dodane et al., "Pharmaceutical applications of chitosan", Pharmaceutical Science & Technology Today, 1998, vol. 1, pp. 246-253.

L. Ilium, "Chitosan and its use as a pharmaceutical excipient", Pharmaceutical Research, 1998, vol. 15, pp. 1326-1331.

B. Wilson et al., "Chitosan nanoparticles as a new delivery system for the anti-Alzheimer drug tacrine", Nanomedicine: Nanotechnology, Biology and Medicine, 2010, vol. 6, pp. 144-152.

A. Richard et al., "Poly(glutamic Acid) for Biomedical Applications", Critical Reviews in Biotechnology, 2001, vol. 21, pp. 219-232.

D. Sgouras et al., "Evaluation of poly(glutamic acid, alanine, tyrosine) (1:1:1) as a lung-specific drug delivery system", STP Pharma Sci., 1994, vol. 4, pp. 87-94.

I. Hajdu et al., "Nanoparticles prepared by self-assembly of Chitosan and poly-γ-glutamic acid", Polymer Science, 2008, vol. 286, pp. 343-350.

Y.H. Lin et al., "Preparation of Nanoparticles Composed of Chitosan/Poly-ç-glutamic Acid and Evaluation of Their Permeability through Caco-2 Cells", Biomacromolecules, 2005, vol. 6, pp. 1104-1112.

S.F. Peng,et al., "Effects of incorporation of poly(g-glutamic acid) in chitosan/DNA complex nanoparticles on cellular uptake and transfection efficiency", Biomaterials, 2009, vol. 30, pp. v1797-v1808.

Z. Keresztessy, et al, "Self-assembling chitosan/poly-γ-glutamic acid nanoparticles for targeted drug delivery" Polymer Science, 2009, vol. 287, pp. 759-765.

S. Santra et al., "Conjugation of Biomolecules with Luminophore-Doped Silica Nanoparticles for Photostable Biomarkers", Analytical Chemistry, 2001, vol. 73, pp. 4988-4993.

P. Tallury et al., "Ultra-small water-dispersible fluorescent chitosan nanoparticles:synthesis, characterization and specific targeting", Chemical Communications, 2009, pp. 2347-2349.

M. Huang et al., "Uptake and Cytotoxicity of Chitosan Molecules and Nanoparticles: Effects of Molecular Weight and Degree of Deacetylation", Pharmaceutical Research, 2004, vol. 21, pp. 344-353.

L. Kong et al., "A study on the bioactivity of chitosan/nano-hydroxyapatite composite scaffolds for bone tissue engineering", European Polymer Journal, 2006, vol. 42, pp. 3171-3179.

V. I. Pedroni et al., "Chitosan structure in aqueous solution", Colloid & Polymer Science, 2003, vol. 282, pp. 100-102.

M. Bodnar et al., "Preparation and Characterization of Chitosan-Based Nanoparticles", Biomacromolecules, 2005, vol. 6, pp. 2521-2527.

R. J. N. Hjerde et al., "Chemical composition of O-(carboxymethyl)-chitins in relation to lysozyme degradation rates", Carbohydrate Polymers, 1997, vol. 34, pp. 131-139.

K. M. Vårum et al., "In vitro degradation rates of partially N-acetylated chitosans in human serum", Carbohydrate Research, 1997, vol. 299, pp. 99-101.

K. Tomihata et al., "In vitro and in tivo degradation of films of chitin and its deacetylated derivatives", Biomaterials, 1997, vol. 18, pp. 567-575.

\* cited by examiner

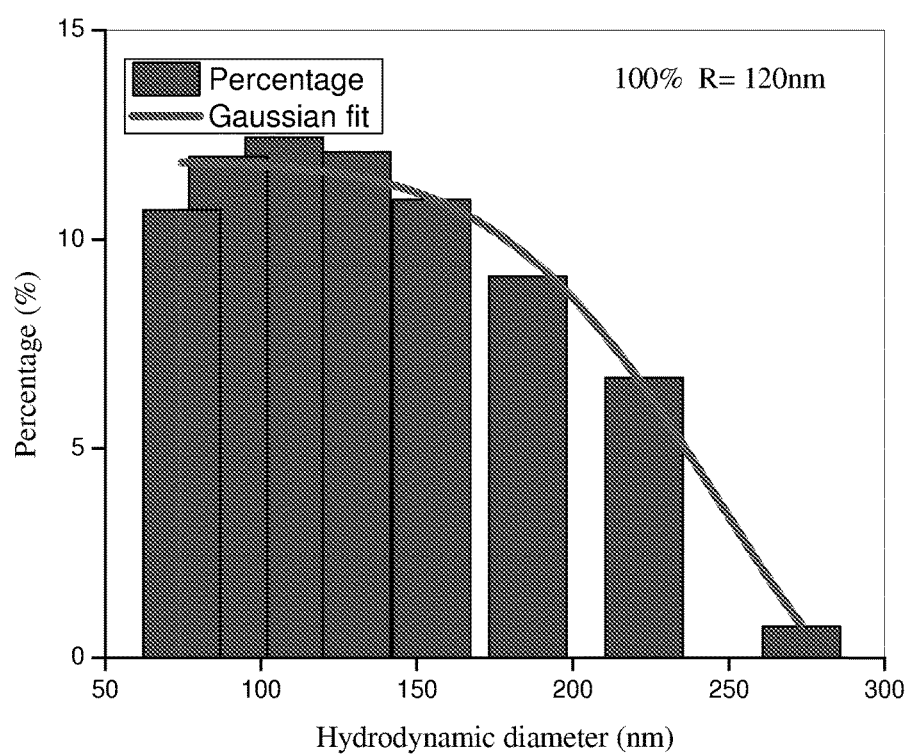
FIG. 3A 1:20in DI water

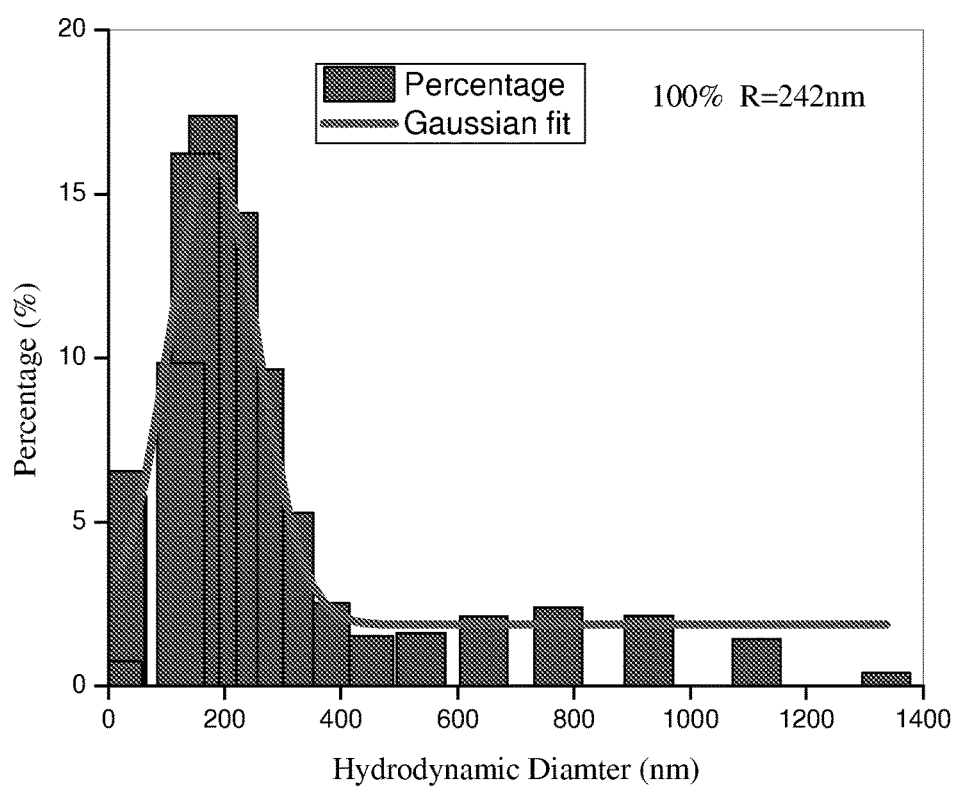
FIG. 3B 1:20 in PBS

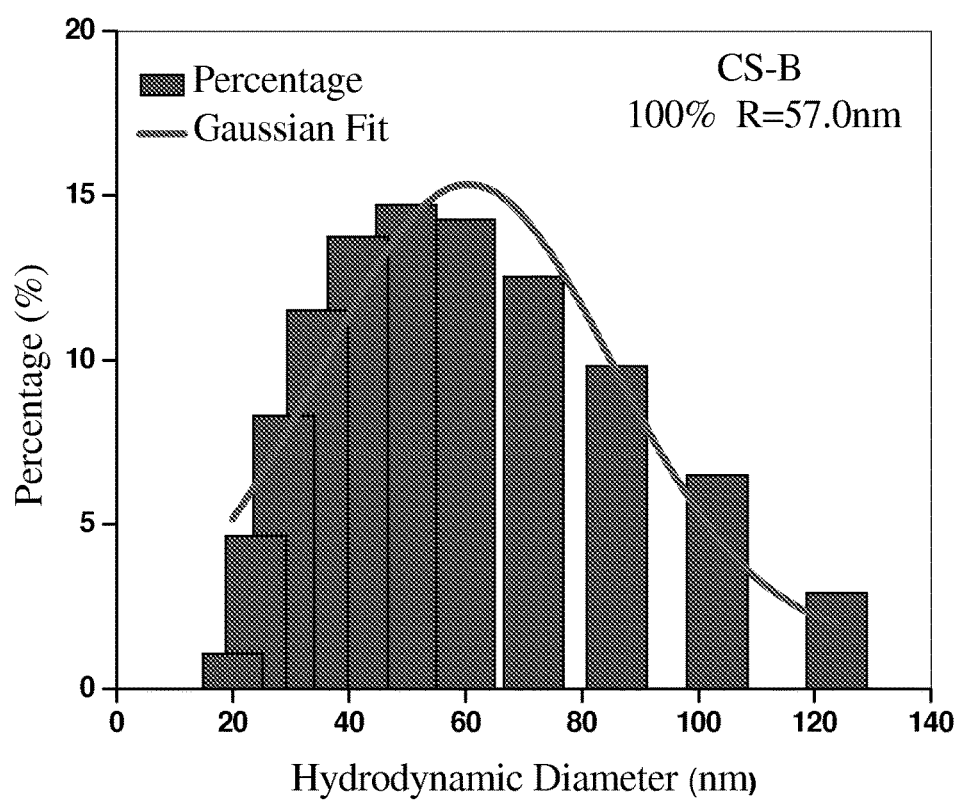
FIG. 3C 1:10 in DI water

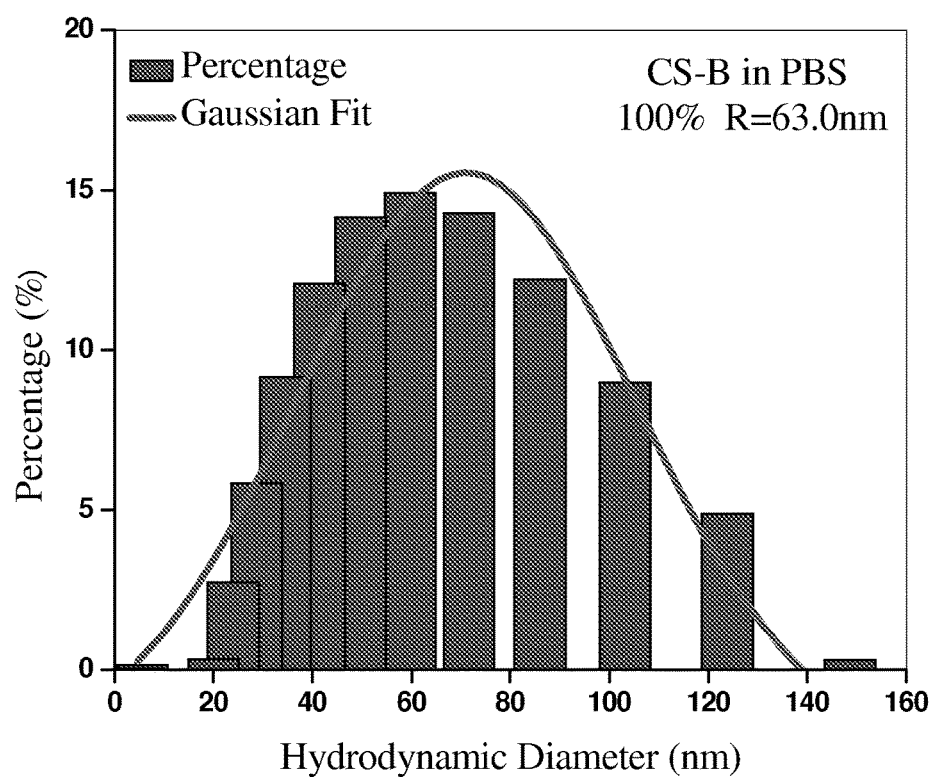
FIG. 3D 1:10 in PBS

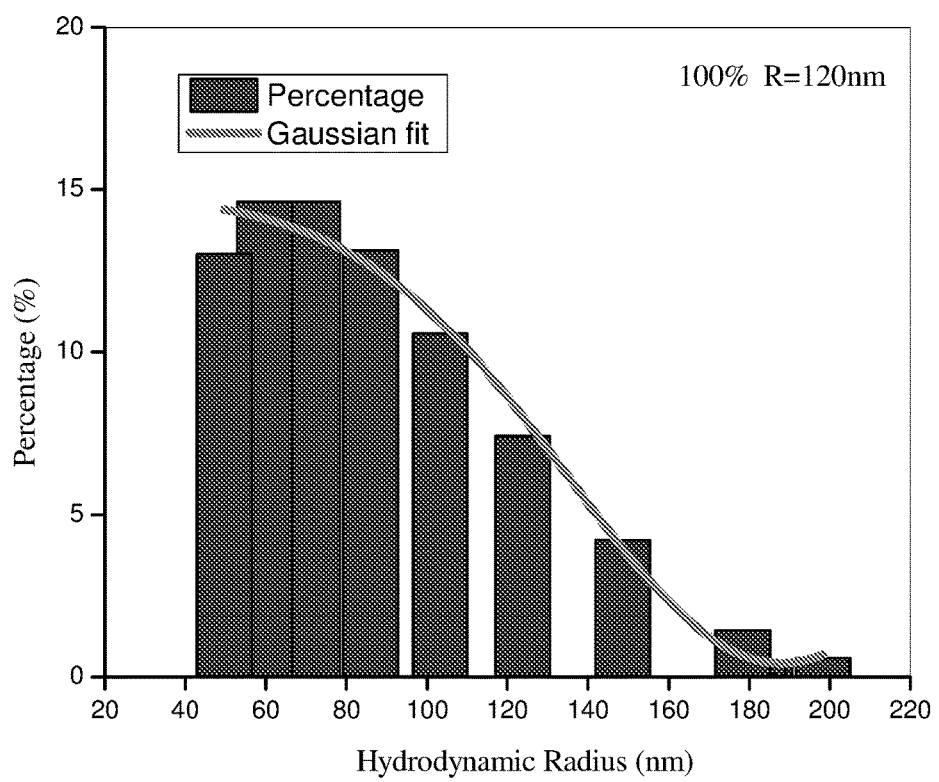
FIG. 3E 1:5 in DI water

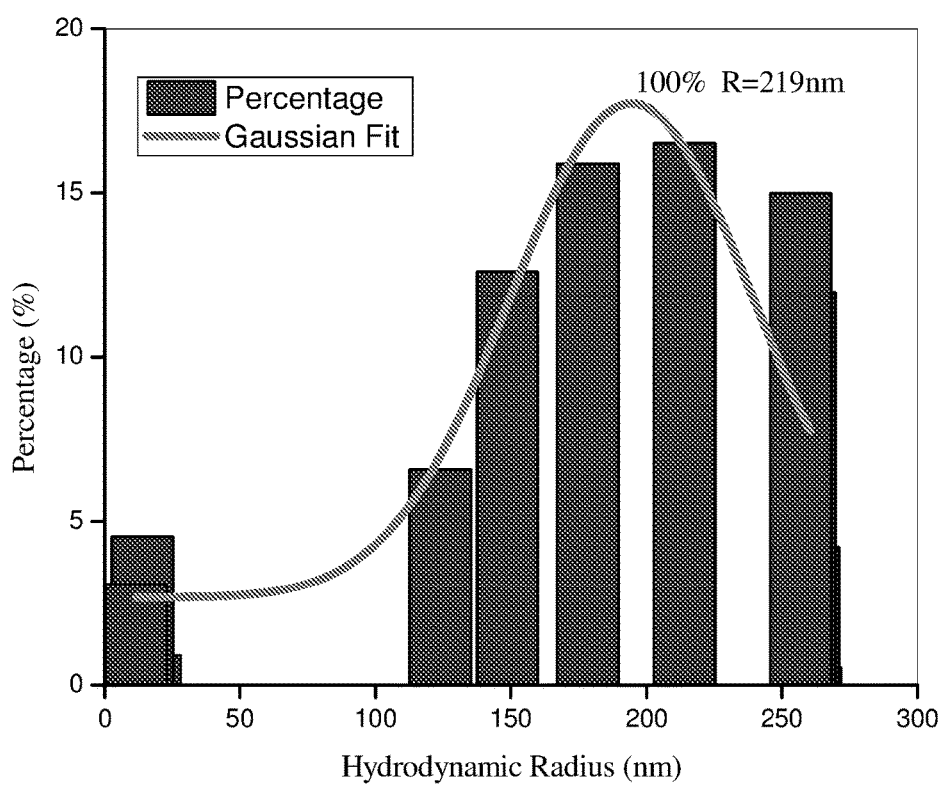
FIG. 3F 1:5 in PBS

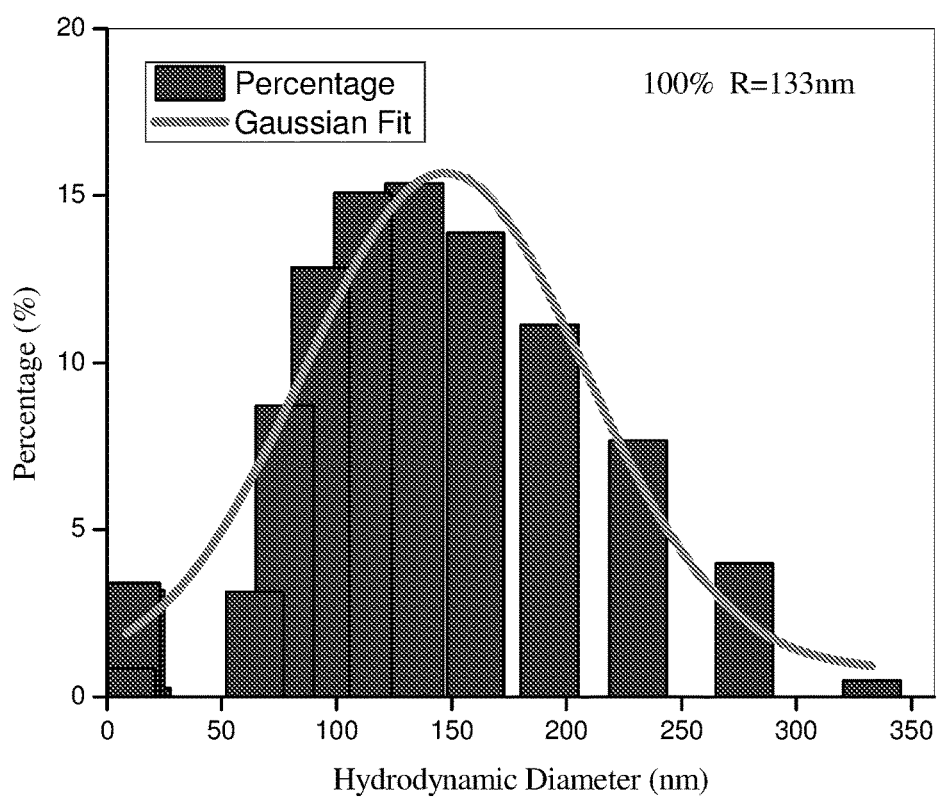
FIG. 3G 1:1 in DI water

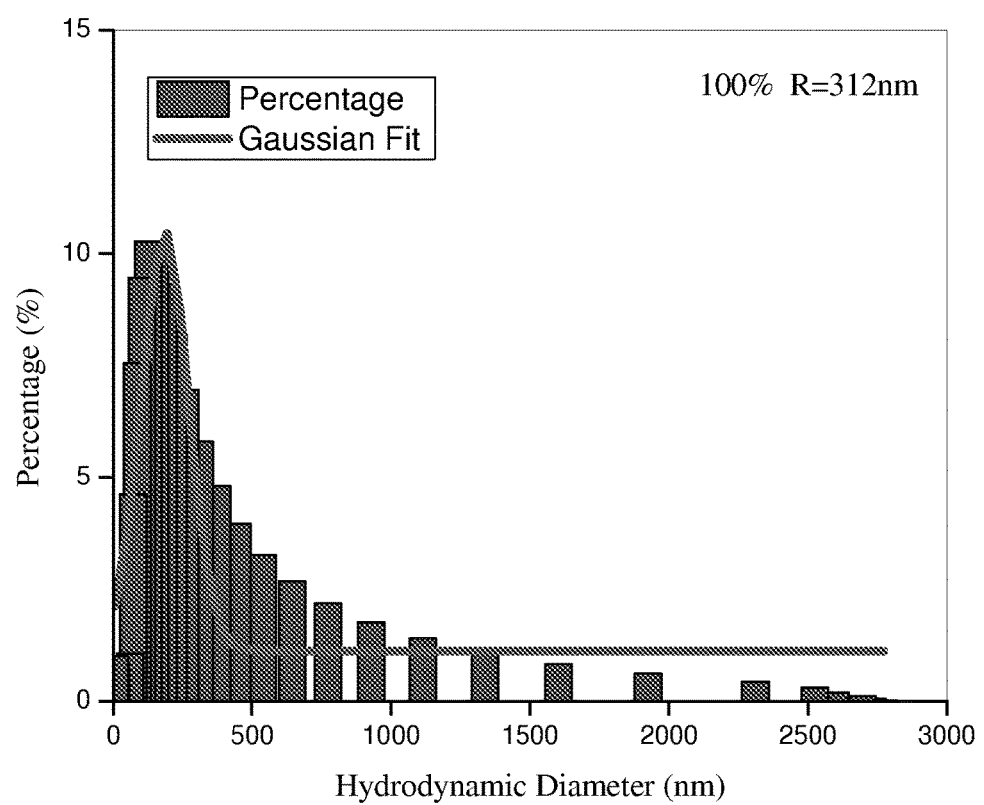
FIG. 3H 1:1 in PBS

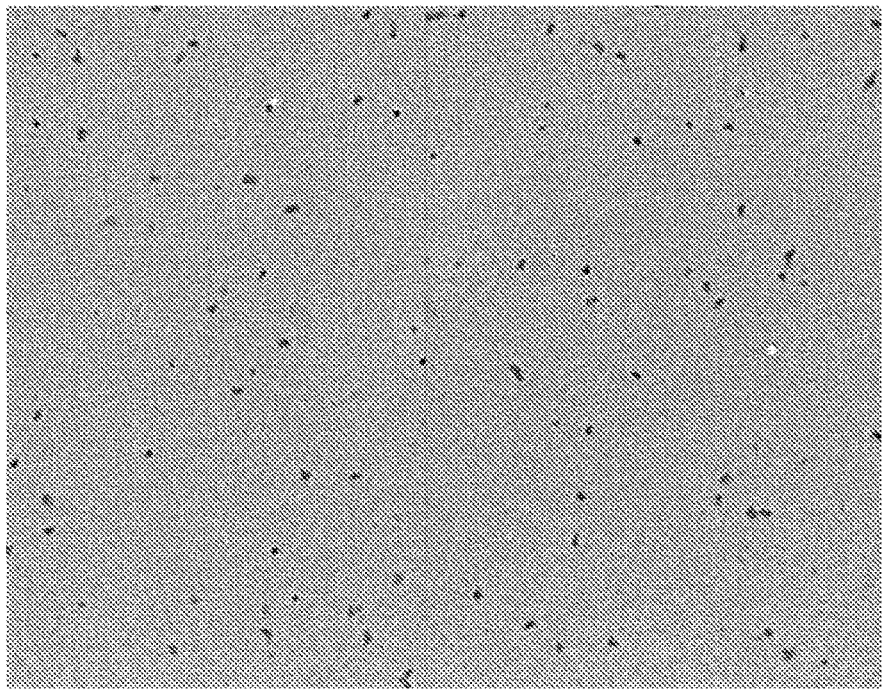
FIG. 7(a) 1:20

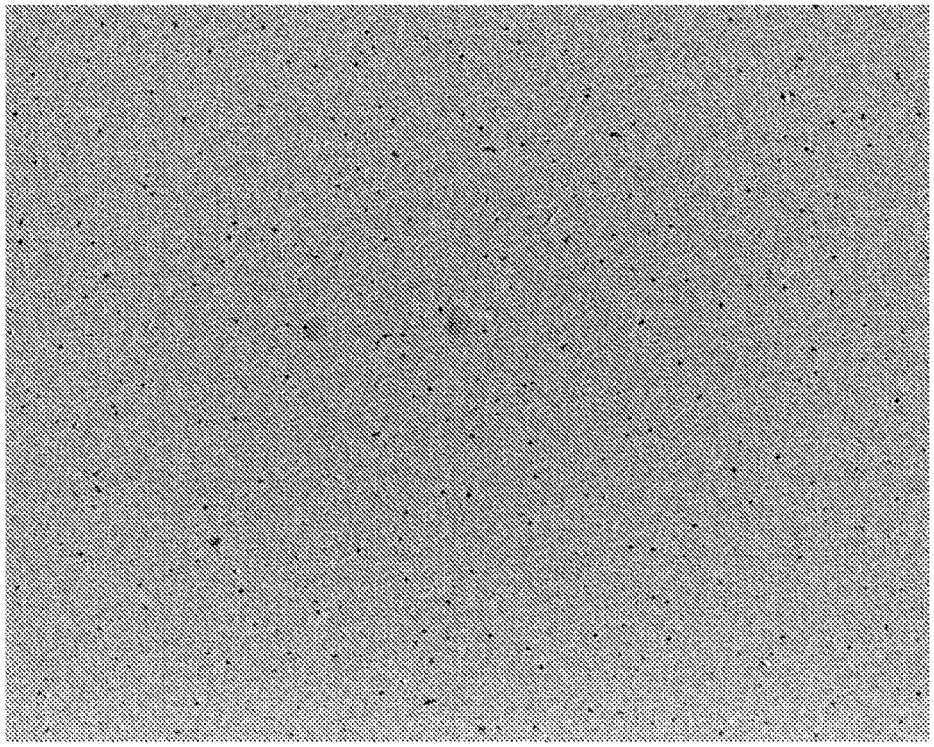
slc.tif 500 nm
Print Mag: 31400x @ 7.0 in HV=100.0kV
15:22 10/26/10 Direct Mag: 4000x
Tilt:
Materials Characterization Facility - UCF
FIG. 7(b) 1:10

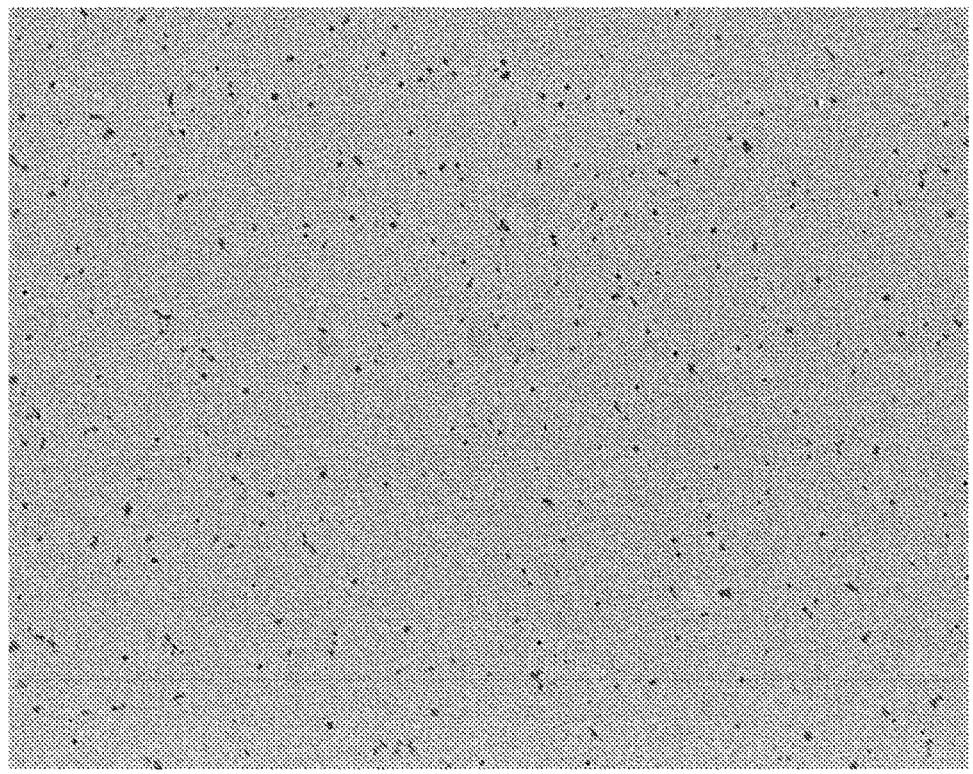
FIG. 7(c) 1:15

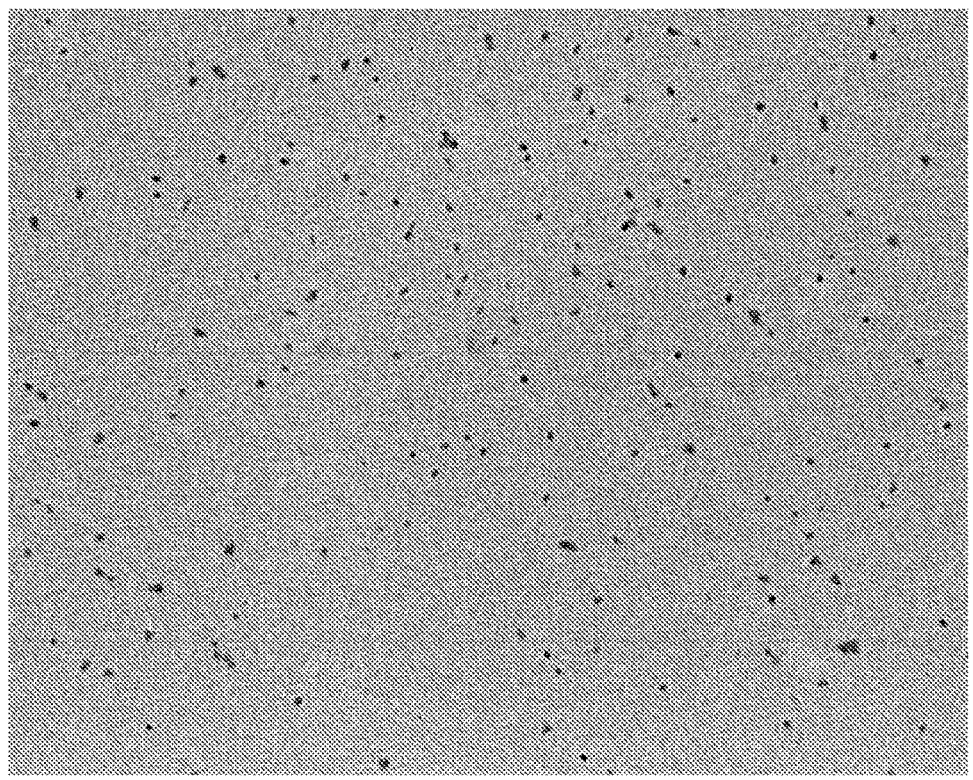
4d.tif
Print Mag: 59500x @ 7.0 in
16:00  10/26/10
500 nm
HV=100.0kV
Direct Mag: 8000x
Tilt:
Materials Characterization Facility - UCF
FIG. 7(d) 1:1

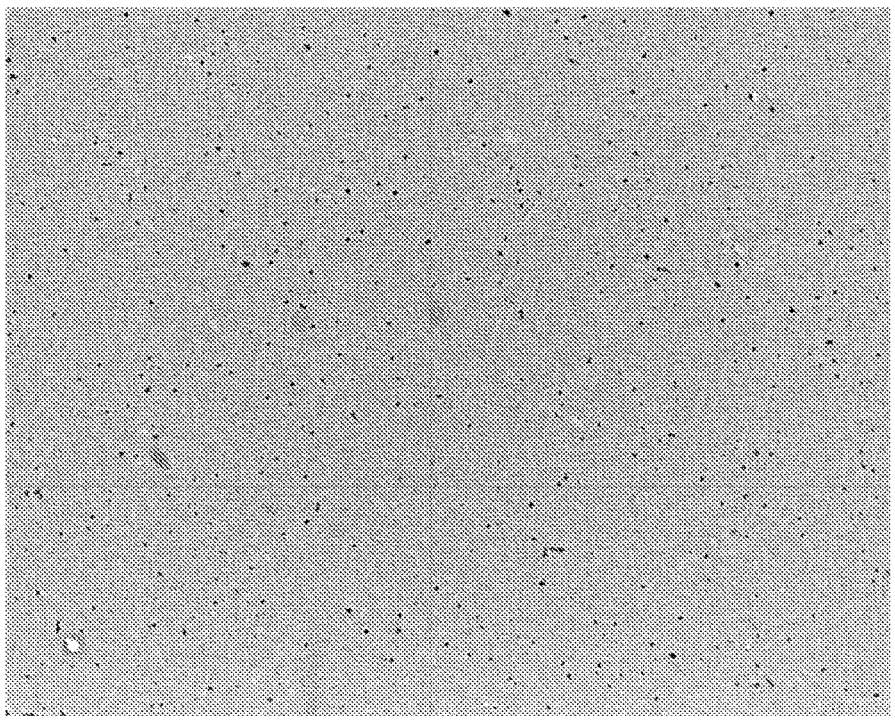
FIG. 8(a) CS NPs

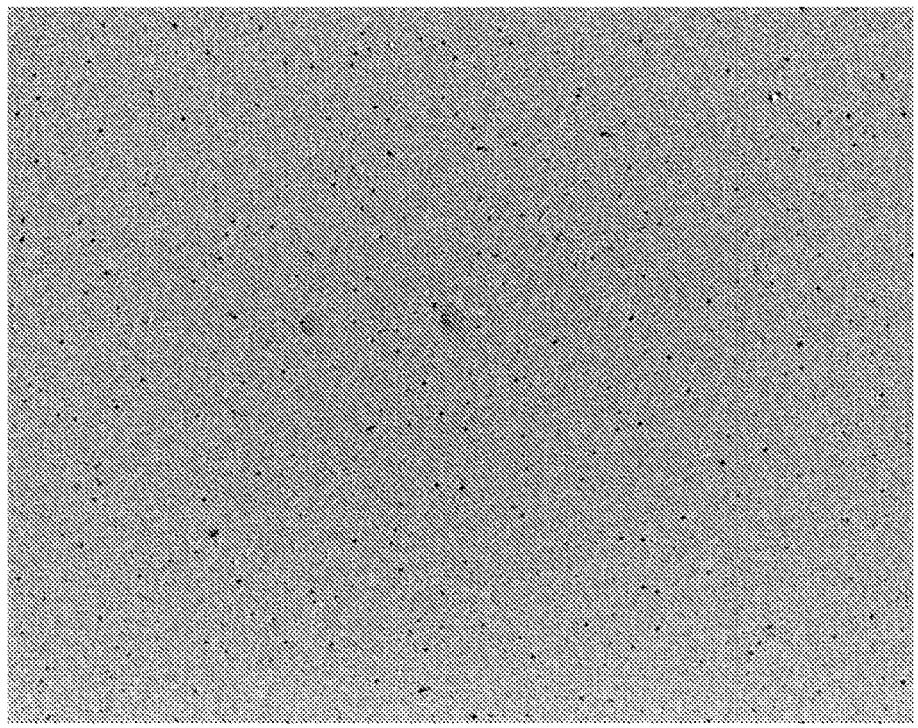
FIG. 8(b) non cross-linked NHPs

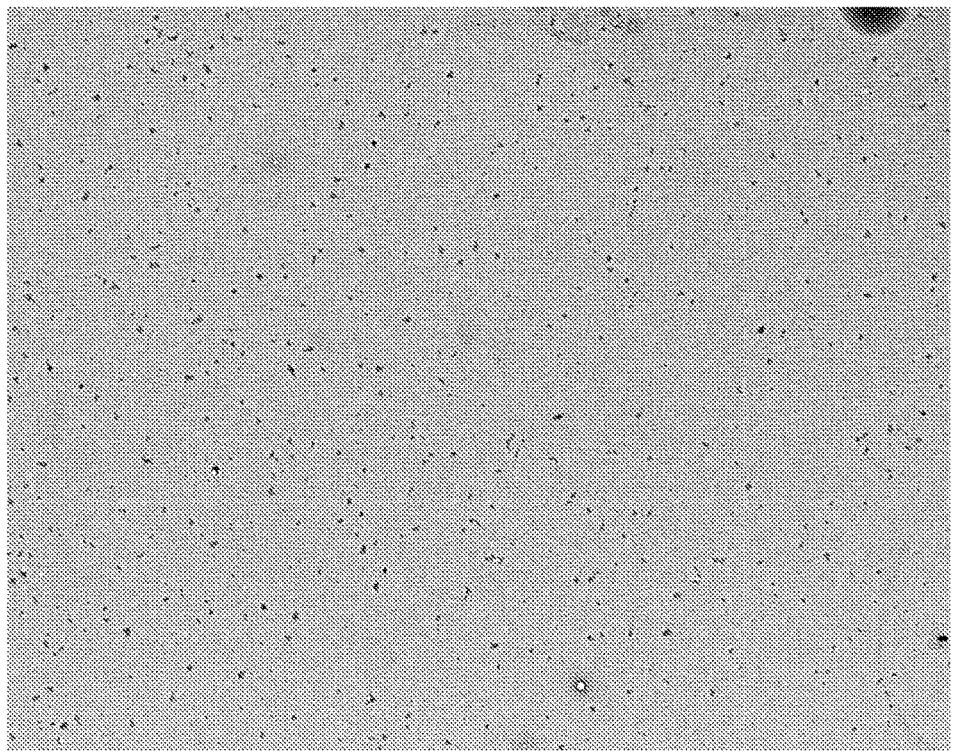
FIG. 8(c) cross-linked NHPs

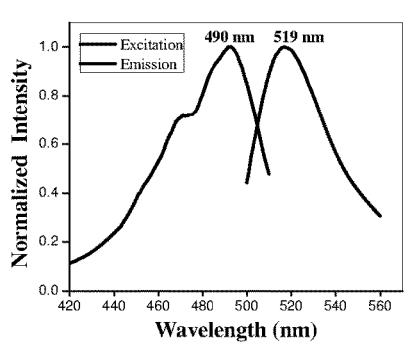 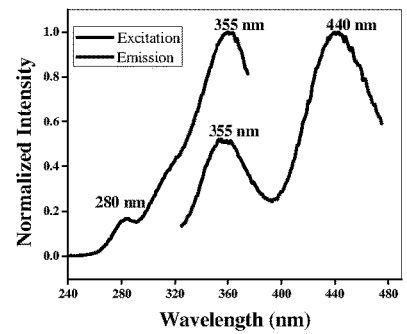
(a)                            (b)
FIGS. 9A-9B
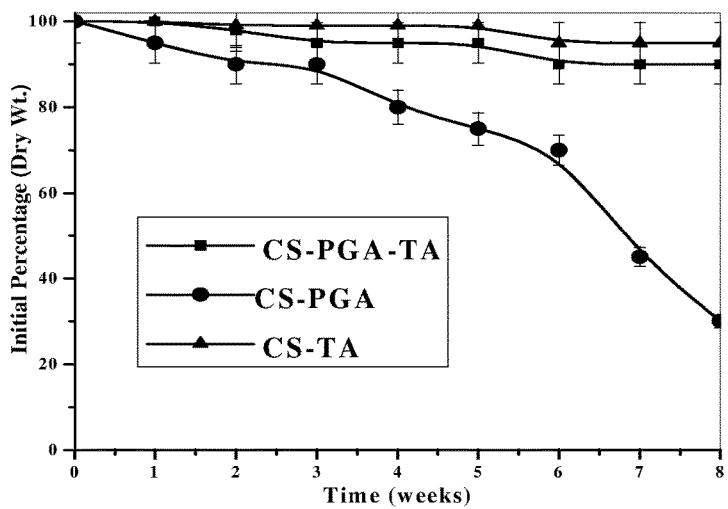
FIG. 10

FIG. 11(a)
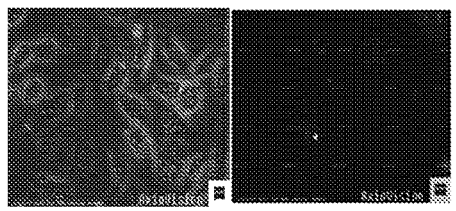
CS-A
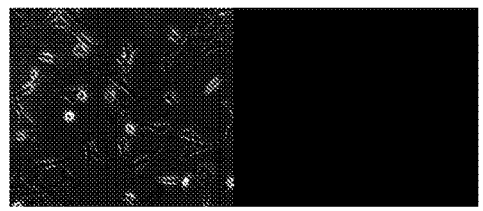
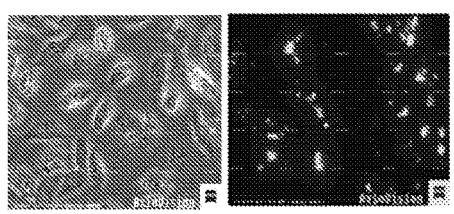
CS-B
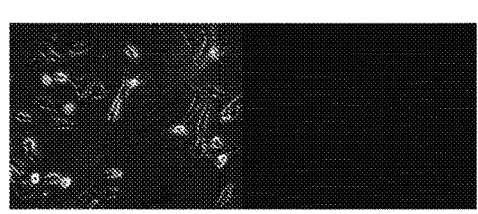
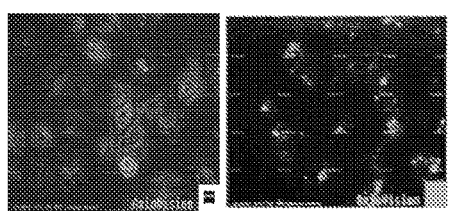
CS-C
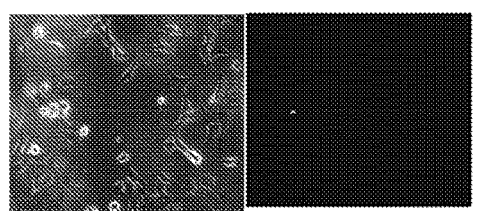
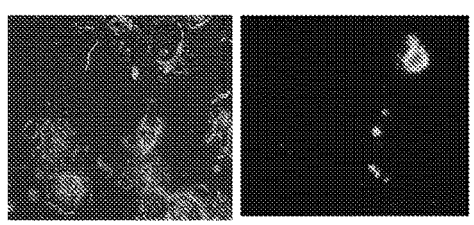
CS-D
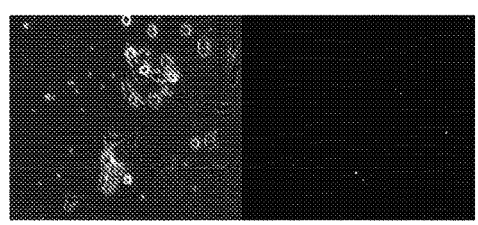
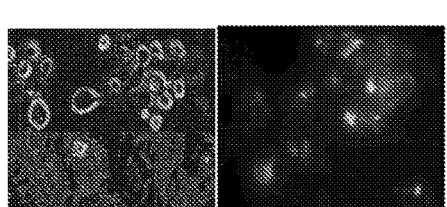
CS-E
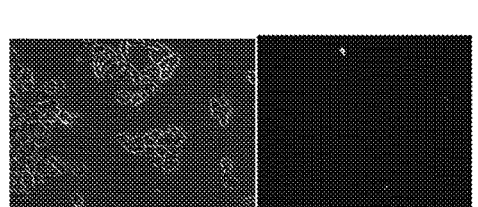
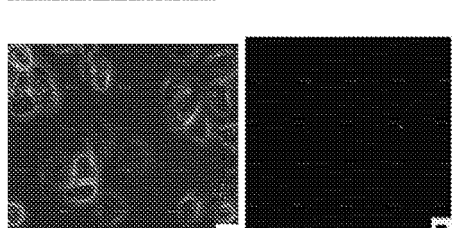
CS-F
FIG. 11(b)

SEQUENCE LISTING

```
<160> NUMBER OF SEQ ID NOS: 1

<210> SEQ ID NO 1
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
atctaactgc tgcgccgccg ggaaaatact gtacggttag a                           41
```

US 9,504,761 B2

STABILIZED CHITOSAN-BASED NANOPARTICLES AND METHODS FOR MAKING THE SAME

STATEMENT OF GOVERNMENT RIGHTS

The work leading to this invention was partly supported by grants from the National Science Foundation (NSF-NIRT Grant No. EEC0506560) and the National Institute of Health (Grant No. 2P01HL059412-11A1). Accordingly, the government may have certain rights in the invention, as specified by law.

SEQUENCE LISTING

The instant application contains a Sequence Listing which has been submitted in ASCII format via EFS-Web and is hereby incorporated by reference in its entirety. Said ASCII copy, created on Aug. 4, 2011, is named 10669089.txt and is 580 bytes in size.

FIELD OF THE INVENTION

The present invention relates to the field of nanoparticles, and more particularly, to chitosan-based nanoparticles stabilized with a hydrophilic dispersing agent, such as polyglutamic acid (PGA).

BACKGROUND OF THE INVENTION

Nanoparticles in general are known to improve drug pay-load and facilitate targeted drug delivery. In this context, chitosan-based (CS) nanoparticles have been shown to be useful as imaging and therapeutic drug/gene delivery systems. It is, however, difficult to synthesize nanoparticles with a narrow size distribution, particularly if the nanoparticles are formed from a naturally-occurring polymer like chitosan that has a wide molecular weight distribution. It is thought to be even more challenging to obtain buffer stable CS nanoparticles with suitable surface functional groups. For one, wide applications of CS nanoparticles are limited because of their poor stability at neutral or basic pH, including physiological conditions (pH 7.4). CS nanoparticles tend to agglomerate in phosphate buffer saline solution, which resembles physiological conditions. This agglomeration is a major hindrance for potential use of CS nanoparticles in biomedical applications. Several attempts have been made to improve the solubility and stability of CS nanoparticles, including modifying and/or derivatizing CS polymer chains using water soluble linkages, degrading high molecular weight CS polymers to low molecular weight polymer, or co-polymerization. However, these methods typically include multiple steps, are time consuming and laborious, and generally lead to new chemical moieties with altogether new properties.

BRIEF DESCRIPTION OF THE DRAWINGS

FIGS. 3A-3H show the effect of PGA to chitosan ratios on particle size distribution profiles obtained from dynamic light scattering (DLS) measurements in deionized (DI) water and phosphate buffered saline (PBS).

FIG. 7A-7D show TEM images of HNPs for different PGA:CS ratios: (a) 1:20, (b) 1:10, (c) 1:5; and (d) 1:1.

FIGS. 8A-8C show TEM images of (a) CS nanoparticles (no PGA); (b) non-cross-linked hybrid nanoparticles (chitosan and PGA) (HNPs); and (c) cross-linked HNPs (chitosan and PGA).

FIG. 9A-9C show: (a) characteristic FITC emission at 519 nm (when recorded at 490 nm excitation wavelength) and 490 nm excitation peak (when recorded at 519 nm emission wavelength); and (b) characteristic dual emission of folate (355 nm and 440 nm, when recorded at 280 nm excitation wavelength) and dual excitation peaks located at 280 nm and 355 nm (when recorded at 440 nm emission wavelength).

FIG. 10 shows comparative a biodegradation study using a lysozyme enzyme for CS nanoparticles, non cross-linked HNPs and cross-linked HNPs.

FIGS. 11A-11B show transmission (left panel) and corresponding fluorescence (right panel) images of nanoparticles, CS-A through CS-F for (a) MDA-MB-231 human breast cancer cells and (b) non tumor Te-71 cells. Fluorescence images confirmed receptor mediated uptake of folate conjugated nanoparticles (CS-A through CS-E) over a non-folated nanoparticle control (CS-F).

DETAILED DESCRIPTION OF THE INVENTION

Figure 1:
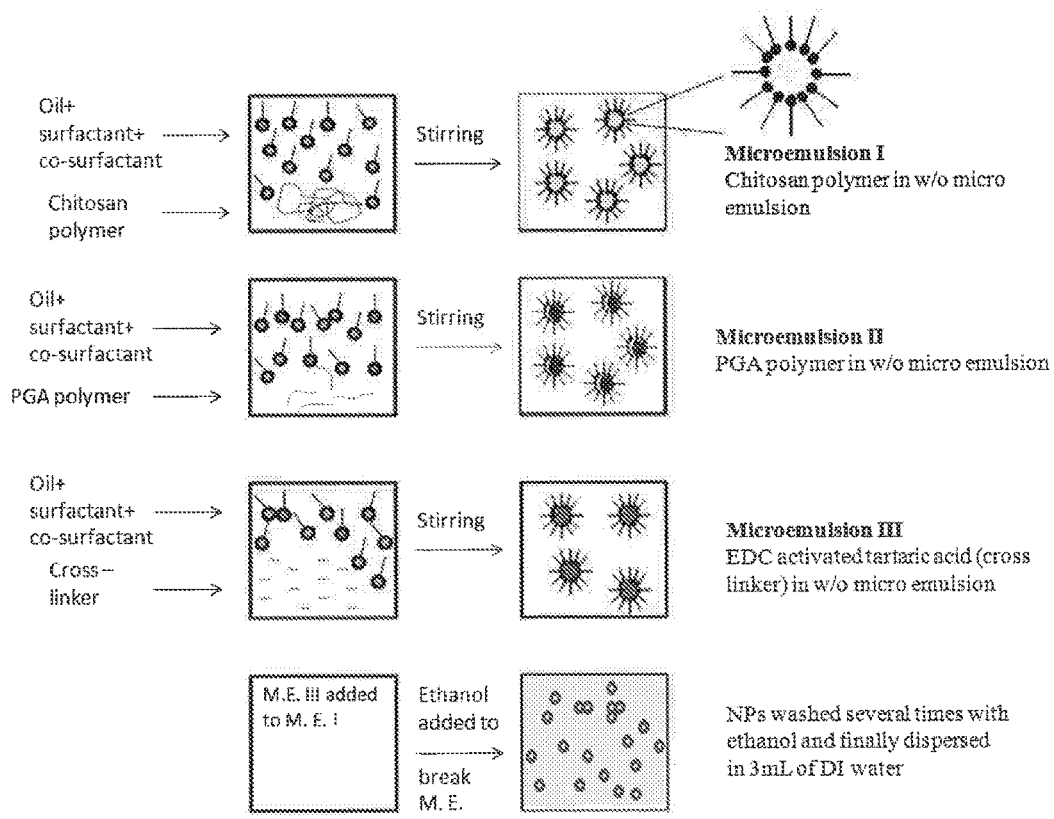
FIG. 1 is an exemplary schematic representation of different W/O microemulsion compositions and methods for the synthesis and purification of chitosan-based nanoparticles, including hybrid (stabilized) chitosan-based nanoparticles (HNPs).

The present inventors have advantageously developed stabilized chitosan-based nanoparticles comprising chitosan polymer and a hydrophilic dispersing agent, e.g., polyglutamic acid (PGA). The stabilized chitosan-based nanoparticles may also be referred to as "hybrid nanoparticles," "HNPs," or "stabilized hybrid nanoparticles" herein. The hydrophilic dispersing agent improves the overall hydrophilicity of the nanoparticles, which improves the stability of the particles at physiological pH conditions, without compromising or altering the size of the nanoparticles. When the hydrophobic dispersing agent is PGA, for example, the negatively charged carboxyl groups of PGA electrostatically interact with positively charged amine groups of the chitosan polymer, thereby resulting in entanglement of the two polymer chains and obviating the need for covalent cross-linking. In the case of PGA, the electrostatic interaction between amine groups of the chitosan polymer and the carboxyl groups of PGA consumes some of the amine groups, thus reducing the overall positive charge on the nanoparticle surface and improving the stability of the nanoparticle. Moreover, chitosan-based nanoparticles with reduced positive surface charges are expected to exhibit insignificant non-specific uptake by target cells.

Even further, the additional functional groups provided by the hydrophilic dispersing agent, e.g., PGA in the nanoparticle system may increase the multimodality and/or multifunctionality of the nanoparticles. For example, in some embodiments, unlabeled HNPs present both carboxyl and amine groups on nanoparticle surface. The presence of more than one type of functional group offers improved flexibility in that more than one type of ligand (e.g. a therapeutic drug, a contrast agent, such as a contrast agent with a modality other than fluorescence) may be conjugated to the HNPs to provide multifunctional particles.

In accordance with one aspect of the present, there is provided a stabilized chitosan-based nanoparticle. The stabilized chitosan-based nanoparticle comprises a chitosan polymer and a hydrophilic dispersing agent. In such a nanoparticle, chains of the chitosan polymer electrostatically interact with chains of the hydrophilic dispersing agent.

In accordance with another aspect of the present invention, the hybrid chitosan-based nanoparticles may be synthesized using water-in-oil (W/O) microemulsion methods described herein, which are capable of forming hybrid nanoparticles having a uniform size distribution. The confined environment of nanometer size water droplet of the W/O microemulsion serves as a nano-reactor and facilitates formation of nearly spherical HNPs via polyelectrolyte complexation.

In one embodiment, there is provided a method for synthesizing stabilized chitosan-based nanoparticles. The method comprises obtaining a first water-in-oil (W/O) microemulsion comprising an oil, a surfactant, and an aqueous phase comprising a chitosan polymer. In addition, the method comprises obtaining a second microemulsion comprising an oil, a surfactant, and an aqueous phase comprising a hydrophilic dispersing agent, e.g., PGA. Further, the method includes reacting components of the first and second microemulsions for a time sufficient to form the stabilized chitosan-based nanoparticles and recovering the stabilized chitosan-based nanoparticles from the reacted first and second microemulsion components. The stabilized chitosan-based nanoparticles have an average particle size of about 100 nm or less.

It is important to an understanding of the present invention to note that all technical and scientific terms used herein, unless defined herein, are intended to have the same meaning as commonly understood by one of ordinary skill in the art. The techniques employed herein are also those that are known to one of ordinary skill in the art, unless stated otherwise. Prior to setting forth the invention in detail and for purposes of more clearly facilitating an understanding the invention as disclosed and claimed herein, the following definitions are provided.

As used herein, the terms "about" and "approximately" as used herein refer to values that are ±10% of the stated value.

As used herein, the term "aptamer" refers to any oligonucleic acid or peptide molecules that is designed or engineered to selectively bind to a specific target molecule.

As used herein, the term "biologically active agent," or "therapeutic drug" refers to any synthetic or natural element or compound, which when introduced into a mammal causes a desired biological response.

As used herein, the terms "bonded," "linked," "labeled," "attached," "conjugated," and variations thereof are intended to be used interchangeably and may refer to covalent, ionic, hydrogen, and/or Van der Waals bonding, for example.

As used herein, the terms "chitosan nanoparticles," "CS NPs" or "CS nanoparticles" are further intended to be used interchangeably and refer to chitosan nanoparticles without a hydrophilic dispersing agent as described herein. These nanoparticles include a cross-linker, typically tartaric acid.

As used herein, the terms "electrostatic interaction" or "electrostatically interact" refer broadly to interactions between charged species.

As used herein, the term "folate" is meant to refer to folic acid, folate, or any derivatives thereof.

As used herein, the terms "stabilized chitosan-based nanoparticles," "hybrid nanoparticles," "stabilized nanoparticles," or "HNPs," are intended to be used interchangeably and refer to stabilized chitosan-based nanoparticles comprising chitosan and a hydrophilic dispersing agent, e.g., PGA, as described above wherein the chains of the chitosan polymer electrostatically interact with chains of the hydrophilic dispersing agent. The term HNPs may refer to such nanoparticles with or without a cross-linking compound; however, the term HNPs is generally used to refer to non cross-linked nanoparticles as the present inventors have found that non cross-linked particles provide advantages suitable for in vivo usage, such as greater biodegradability.

As used herein, the term "hydrophilic" refers to any substance having an affinity for water and tending to dissolve in, mix with, or swell in a water or aqueous medium.

As used herein, the term "hydrophobic" refers to any substance not having an affinity for water and tending not to dissolve in, mix with, or swell in a water or aqueous medium.

As used herein, the term "water soluble" as in a "water-soluble polymer" is any polymer that is soluble in water at room temperature. The water-soluble polymer is a polymer having a solubility of 1% (w/v) or more in water at 25° C. Typically, a water-soluble polymer will transmit at least about 75%, such as at least about 95%, of light transmitted by the same solution after filtering. On a weight basis, a water-soluble polymer will often be at least about 35% (w/v) soluble in water, such as at least about 50% (w/v) soluble in water, at least about 70% (w/v) soluble in water, or at least about 85% (w/v) soluble in water, at 25° C. Typically, the water-soluble polymer is at least about 95% (w/v) soluble in water or completely soluble in water.

As used herein, the term "water-in-oil emulsion" means that the dispersed phase, e.g., water phase, is a phase consisting of discrete parts fully surrounded by material of another phase, e.g., an oil phase.

As used herein, the terms "chitosan" or "chitosan polymer" refer to chitosan (also known as poliglusam, deacetylchitin, poly-(D)glucosamine) and any derivatives thereof. The chitosan polymer is typically composed of a linear polysaccharide of randomly distributed β-(1-4)-linked D-glucosamine (deacetylated unit) and/or N-acetyl-D-glucosamine (acetylated unit) units. The general terms "chitosan" or "chitosan polymer" as used herein may also refer to chitosan or chitosan having one or more molecules attached thereto, e.g., bonded, or conjugated, thereto, such as an imaging agent, a target-specific ligand, or a biologically active compound.

Exemplary derivatives of chitosan include trimethylchitosan (where the amino group has been trimethylated) or quaternized chitosan. Advantageously, chitosan has a plurality of amine functional groups, which as set forth below, may be utilized for the attachment of various agents thereto, such as imaging agents, target-specific ligands, and/or biologically active agents.

Chitosan is typically produced by deacetylation of chitin, which is the structural element in the exoskeleton of crustaceans (crabs, shrimp, etc.) and cell walls of fungi. One known method for the synthesis of chitosan is the deacetylation of chitin using sodium hydroxide in excess as a reagent and water as a solvent. The degree of deacetylation (% DD) can be determined by NMR spectroscopy, and the % DD in chitosan for use in the methods described herein may be in the range of from 20-100%, and typically from 60-100%. This reaction pathway, when allowed to go to completion (complete deacetylation), yields up to 98% product. The amino group in chitosan has a pKa value of ~6.5, which leads to a protonation in acidic to neutral solution with a charge density dependent on pH and the % DD value. Chitosan is water-soluble, is useful as a bioadhesive, may enhance the transport of polar drugs across epithelial surfaces, is biocompatible, and is critically biodegradable. In one embodiment, the chitosan has a molecular weight of from about 50,000 to about 190,000 daltons.

As used herein, the term "surfactant" refers to a wetting agent that lowers the surface tension of a liquid, thereby allowing easier spreading and the lowering of the interfacial tension between two liquids.

Surfactants are typically classified into four primary groups; anionic, cationic, nonionic, and zwitterionic (dual charge). The head of an ionic surfactant carries a net charge. If the charge is negative, the surfactant is called anionic; if the charge is positive, it is called cationic. If a surfactant contains a head with two oppositely charged groups, it is termed zwitterionic. In one embodiment, the surfactant comprises a nonionic surfactant. A nonionic surfactant refers to a surfactant in which the hydrophilic head group is uncharged.

In particular embodiments, the surfactant for the first and/or second microemulsion comprises Triton X-100. As used herein, the term "Triton X-100" refers to an octylphenol ethylene oxide condensate (P-octyl polyethylene glycol phenyl ether). Triton X-100 is commercially available from Union Carbide, USA or Sigma-Aldrich, USA, for example. The "X" series of Triton detergents are produced from octylphenol polymerized with ethylene oxide. The number ("–100") relates only indirectly to the number of ethylene oxide units in the structure. X-100 has an average of 9.5 ethylene oxide units per molecule, for example. Alternatively, the surfactant may be any other suitable surfactant material, such as a fatty acid ester, a polyglycerol compound, a polyoxyethylene surfactant, e.g., as Brij-30, Brij-35, Brij-92, Tween-20, and/or Tween-80. In one embodiment, the first and/or second microemulsion also comprises a co-surfactant. The co-surfactant is typically a different surfactant or compound from the primary surfactant used. In one embodiment, the co-surfactant comprises n-hexanol. N-hexanol is believed to stabilize the interface between oil and water along with the primary surfactant. In another embodiment, the co-surfactant comprises sodium bis(2-ethylhexyl) sulfosuccinate (docusate sodium), also sold commercially as Aerosol® OT (AOT).

The oil may be any hydrophobic compound, such as one that is immiscible with water, e.g., aliphatic and aromatic hydrocarbons. Non-limiting examples of suitable oils for use in the present invention, e.g. in the first and second microemulsions, include aliphatic and aromatic hydrocarbons, e.g., hexane, heptane, cyclohexane, toluene and benzene. In a particular embodiment, the oil comprises cyclohexane.

The water (aqueous phase) to surfactant molar ratio in each microemulsion may be any suitable ratio appropriate for the particular materials and application, such as from about 2:1 to about 70:1, and in a particular embodiment about 22:1. A non-limiting typical example of a W/O ternary microemulsion system comprises cyclohexane (11.0 mL), n-hexanol (4.0 mL), water (total volume of aqueous phase, 4.0 mL) and TX-100 (neat, as received from Sigma-Aldrich; 6.0 mL). See *Chem. Commun.*, 2009, 2347-2349, supp document.

The hydrophilic dispersing agent may be any compound having repeating structural units that have one or more functional groups that will interact by electrostatic or charge attraction (or otherwise) with the amine functional groups of the chitosan polymer. In one embodiment, the hydrophilic dispersing agent is a polymer other than chitosan having repeating structural units, wherein each of the structural units includes one or more carboxyl groups. In a particular embodiment, the hydrophilic dispersing agent comprises PGA or any structural analogues or derivatives thereof. One of the advantages of utilizing PGA as the hydrophilic dispersing agent includes the fact that PGA is a negatively charged biocompatible and biodegradable natural polymer, rendering it suitable for in vivo applications. Similarly, PGA increases the overall hydrophilicity of the chitosan-based nanoparticles, thus improving the stability of the nanoparticles having PGA therein at physiological pH conditions (e.g., pH 7.4). Further, PGA provides additional functional groups to incorporate additional functionality and/or modalities to the nanoparticles, such as the attachment of imaging agents, targeting agents, and/or bioactive compounds to the nanoparticles. Even further, the incorporation of PGA in the nanoparticles likely reduces the positive surface charge on each of the chitosan-based nanoparticle's surface (relative to a chitosan-based nanoparticle without the PGA), which likely aids in reducing non-specific uptake by cells.

Alternatively, the hydrophilic dispersing agent may comprise or further comprise any other compound that will increase the hydrophilicity of the chitosan-based particle relative to a nanoparticle without the hydrophilic dispersing agent. In other embodiments, for example, the hydrophilic dispersing agent may comprise one or more of PEG (polyethylene glycol), m-PEG, PPG (polypropylene glycol), m-PPG, polysialic acid, polyaspartate, polylysine, polyethyleneimine, biodegradable polymers (e.g., polylactide, polyglyceride), and functionalized PEG, e.g., terminal-functionalized PEG, analogues, derivatives, or combinations thereof of the above compounds.

With the hydrophilic dispersing agent, no pH restrictions are generally required prior to W/O microemulsion synthesis. In one embodiment, the aqueous phase comprising chitosan is maintained at a pH below about 6.5, although the present invention is not so limited. At higher pH's, the chitosan polymer will tend to precipitate. Further, in one embodiment, the hydrophilic dispersing agent comprises PGA and any aqueous phase comprising PGA is maintained at a pH of from about 4 to about 9, e.g., a pH of about 7, although the present invention is not so limited. In one embodiment, the aqueous solution comprising chitosan is prepared in acidic solution (1% acetic acid or 1% mineral acid) followed by dialysis.

When the microemulsions comprising the hydrophilic dispersing agent and the chitosan are mixed, the two chemical entities self-assemble to form complex network structures due to electrostatic interactions between the amine groups of chitosan and functional groups of the hydrophilic dispersing agent. Typically, the amine groups of the chitosan polymer are positively charged and interact with negatively charged functional groups, e.g., carboxyl groups, on the hydrophilic dispersing agent, e.g., PGA. In addition to the selection of the a chitosan polymer and a hydrophilic dispersing agent generally, one skilled in the art would appreciate that the formation and stability of the nanoparticles may be further determined by several factors, including but not limited to, the concentration of each polymer, molecular weights of the polymers, degree of ionization, charge density of polymers, charge distribution over the polymeric chains, the molar ratio of the two polymers, or combinations thereof.

In accordance with another aspect of the invention, the present inventors have surprisingly found that a molar ratio of hydrophilic dispersing agent to chitosan from about 1:1 to about 1:20 provides excellent stability and integrity for the stabilized chitosan-based nanoparticles. Further, nanoparticles with a hydrophilic dispersing agent:CS ratio of 1:10 were shown to exhibit the best dispersibility at physiological conditions, e.g., in phosphate-buffered saline (PBS) solution (pH about 7.4). Notably also, the stabilized chitosan-based nanoparticles (HNPs) were found to not increase in nanoparticle size when added to deionized water and PBS solutions, thereby maintaining their advantageously narrow and relatively small size range even in solution.

It is appreciated that the stability of particles in solution is likely determined by various factors such as particle size, surface charge and hydrophilicity. For example, the relatively high degree of stability of the hybrid nanoparticles in DI water and PBS may be attributable to several factors, which may be mutually exclusive or not, including: particle size (greater mobility), surface charge (positive zeta potential), hydrophilicity, salt concentration, hydrophilic polymeric surface (steric repulsion) and presence of large number of hydrophilic domains (solvated sites in the entire particle).

While not wishing to be bound by theory, it is believed that the hydrophilic dispersing agent disrupts particle-particle interaction, which prevents agglomeration of adjacent nanoparticles, as well as provides a high degree of stability and particle integrity to the nanoparticle. PGA, for example, is a highly hydrophilic water-soluble polymer containing carboxylate groups in its backbone. Chitosan nanoparticles are generally not stable in PBS (phosphate buffer saline; pH 7.4, physiological pH condition) due to passivation of positive surface charge (amines) by the phosphate ions. It is noted that chitosan polymer tends to precipitate in water if the solution pH is above about 6.3 due to neutralization of protonated amine groups. The present inventors have found that the stability of chitosan nanoparticles in buffer may be greatly improved by adding a hydrophilic dispersing agent as described herein, e.g., PGA. PGA increases overall particle hydrophilicity (hydrated shell around particle) and populates negatively charged carboxylate groups on particle surface. Generally, there must be a balance between the particle surface charge and hydrophilicity. A relatively high PGA to CS molar ratio (1:5 or 1:1) reduces surface charge below a critical value (+30 mV approximately), increasing turbidity due to particle-particle sticky interaction (resulting particle agglomeration). In a particular embodiment, the inventors have surprisingly also found that when the hydrophilic dispersing agent is PGA, a molar ratio of about a 1:10 PGA to chitosan provides a nanoparticle that shows exceptional stability and particle integrity.

Figure 6:
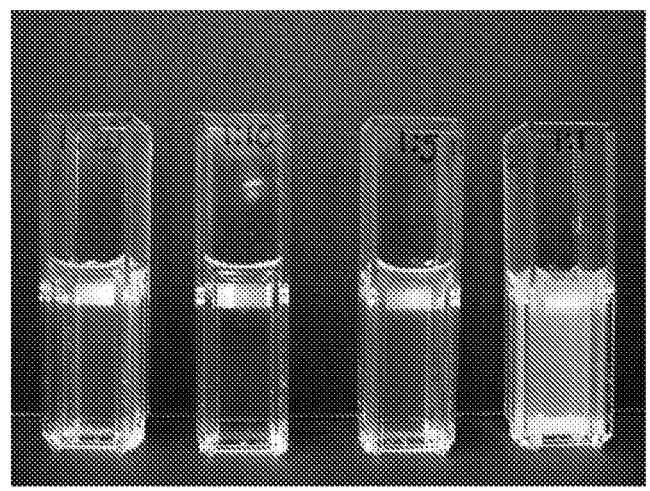
FIG. 6 is a digital image of HNPs solutions for different PGA:CS ratios (1:20, 1:10, 1:5, and 1:1).

The stability and integrity of the stabilized chitosan-based nanoparticles may be determined by transmittance or turbidity measurements as are known in the art. As shown in FIG. 6, nanoparticles having about a 1:10 PGA:CS molar ratio are relatively stable and provide a highly transparent solution (about 99% transmittance). As is also shown in FIG. 6, at lower or higher PGA:CS molar ratios, the solutions become increasingly turbid with a maximum turbidity at about a 1:1 (about 1:20, 1:10, 1:5, and 1:1 left to right in FIG. 6). In one embodiment, the stabilized chitosan-based nanoparticles have a transmittance value of at least about 90% at a physiological pH, such as a pH of about 7.4 or less.

It is further noted that the hydrophilic dispersing agent helps maintain the stability and the integrity of the compartmentalized chitosan nanoparticles without the need for cross-linking. In a sense, during synthesis of the nanoparticles described herein, the water droplet size determines the particle size of the formed nanoparticle and the electrostatic interaction between the chitosan polymer and the hydrophilic dispersing agent maintains the integrity of the nanoparticle, e.g., the nanoparticle does not break apart. The present inventors have found that the non cross-linked stabilized chitosan-based nanoparticles are especially suitable for use in pH 7.4 and would thus be expected to have increased bioavailability at pH 7.4 than cross-linked counterparts. Moreover, due to the absence of cross-linking, it is expected that non cross-linked nanoparticles would be more biodegradable than their cross-linked counterparts. Accordingly, in one embodiment, the stabilized chitosan-based nanoparticles are free from a cross-linker or cross-linking compound.

As set forth above, in one embodiment, the method for synthesizing stabilized chitosan-based nanoparticles comprises obtaining a first W/O microemulsion comprising an oil, a surfactant, and an aqueous phase having a chitosan polymer. The first microemulsion may be obtained by combining the above components under stirring conditions for at least a few minutes, e.g., five minutes. In one exemplary embodiment, the first microemulsion may be formed by the dropwise addition of Triton X-100 to a mixture of the cyclohexane, n-hexanol, and the chitosan polymer. Upon stirring for about an hour, a yellow-colored, stable, completely transparent microemulsion may be formed.

In addition, the method comprises obtaining a second microemulsion comprising an oil, a surfactant, and an aqueous phase comprising a hydrophilic dispersing agent, e.g., PGA. The second microemulsion may be obtained by combining the above components under stirring conditions for at least a few minutes, e.g., five minutes. In one exemplary embodiment, the second microemulsion may be formed by the addition, preferably dropwise, of Triton X-100 to a mixture of the cyclohexane, n-hexanol, and the hydrophilic dispersing agent over a time period, such as about an hour.

After the first and the second microemulsions are formed, the second microemulsion may be added, preferably dropwise, to the first microemulsion and stirred to react components of the first and second microemulsions together to form the stabilized chitosan-based nanoparticles. After the addition is finished, the microemulsions may be continuously mixed by stirring for a suitable period of time, e.g., 2-24 hours, to ensure a complete reaction. Dark conditions may be required for synthesis that involves fluorescein isothiocyanate (FITC) or iohexyl, otherwise normal room light conditions are typically maintained during stirring.

Thereafter, the formed stabilized chitosan-based nanoparticles may be recovered from the reacted first and second microemulsions by any suitable method known in the art. In one embodiment, the stabilized chitosan-based nanoparticles are recovered after the reacting by the addition of ethanol so as to separate the nanoparticles from the microemulsion. The addition of the ethanol destabilizes the microemulsion system resulting in the precipitation of the nanoparticles from the microemulsion. In one embodiment, the ethanol may comprise a 95% (V/V) ethanol solution. After reacting and recovering the stabilized chitosan-based nanoparticles, the method may further comprise washing the recovered nanoparticles in ethanol at least once, followed by suspending the recovered stabilized chitosan-based nanoparticles in a fluid carrier, such as water. In order to further clean the particle suspension, the suspended recovered nanoparticles may be further dialysed against water. Dialysis is the process of separating molecules in solution by the difference in their rates of diffusion through a semipermeable membrane, such as dialysis tubing.

In one embodiment, in the washing step, the stabilized chitosan-based nanoparticles may be pelleted by centrifugation at 8000 rpm in an Eppendorf, model 5810R, angle-head centrifuge, for example, in about a 35 ml total volume for about 15 minutes. Those skilled in the art will be able to determine centrifugation conditions necessary for pelleting these nanoparticles in other centrifuge systems. Further, in the washing step, ethanol may be added to the centrifuged nanoparticles followed by vortexing for a few minutes and then sonication (using a sonic bath) for about 10 seconds. This allows nanoparticles to re-disperse uniformly in the ethanol. This ethanol solution may then be centrifuged for about 15 minutes. Nanoparticles at this stage typically settle down at the bottom of the centrifuge tube. The supernatant may then be discarded. This washing procedure (addition of ethanol to the centrifuged nanoparticles, vortexing the solution followed by sonication, centrifugation and removal of the supernatant) may be repeated multiple times, e.g., five times. Washed nanoparticles may be re-suspended in a fluid carrier, preferably water, and aggregated nanoparticles may be separated from monodispersed nanoparticles by filtration.

In certain aspects of the present invention, either or both of the chitosan polymer and the hydrophilic dispersing agent may be labeled with one or more additional ligands, such as an imaging agent, a ligand having an affinity for a specific target, and/or a biologically active agent to form chitosan-based nanoparticles having such additional moieties or compounds incorporated therein. In one embodiment, the additional ligand(s) may be linked to the chitosan polymer prior to the reacting of the components of the first microemulsion and the second microemulsion, although it is understood that the present invention is not so limited. It is contemplated that the additional ligands described herein may be linked to the chitosan polymer by bonding, covalent or otherwise, through the amine groups of the chitosan polymer, although the invention is not so limited.

In another embodiment, the additional ligand is bonded to the hydrophilic dispersing agent through compatible functional groups on the hydrophilic dispersing agent. For example, when the hydrophilic dispersing agent is PGA, the additional ligand may be bonded to the PGA polymer through its amine or carboxyl functional groups. In some embodiments, spacer molecules or coupling agents may be utilized between the ligand to be attached and the chitosan polymer or the hydrophilic dispersing agent.

In accordance with one aspect of the present invention, either or both of the chitosan polymer or the hydrophilic dispersing agent is labeled with an imaging agent. For example, the imaging agent may comprise one or more of a fluorophore, iohexyl, and a paramagnetic chelate having a paramagnetic ion bound therein. In one embodiment, the chitosan polymer is labeled with a fluorophore. In another embodiment, the chitosan polymer may be labeled with a fluorophore and also a paramagnetic chelate (chelator) having an MRI (magnetic resonance imaging) contrast agent bound therein linked to the chitosan polymer so that the recovered stabilized chitosan-based nanoparticles are effective as a bimodal agent that is fluorescent as well as paramagnetic. The MRI contrast agent may comprise a paramagnetic ion selected from one or more of gadolinium, dysprosium, europium, and compounds, or combinations thereof, for example. In one embodiment, the paramagnetic ion comprises a gadolinium ion and the chelator is a DOTA-NHS ester (2,2',2''-(10-(2-(2.5-dioxopyrrolidin-1yloxy)-2-oxoethyl)-14,7,10-tetraazacyclododecane-1,4,7-tryl)triaceticacid). $Gd^{3+}$ ions are paramagnetic and DOTA is a chelator of Gd ion. The Gd-DOTA is paramagnetic agent and it provides MRI contrast. Gd-DOTA is commercially available under the brand name ProHance® (also called Gadoteridol). In another embodiment, either or both of the chitosan polymer or the hydrophilic dispersing agent may be solely or additionally linked with iohexyl such that the recovered nanoparticles are radio-opaque.

When a fluorophore is provided, the fluorophore may comprise at least one of a fluorescent dye, a quantum dot (Qdot), a bioluminescence agent, or combinations thereof. Exemplary bioluminescent agents include a luciferase enzyme and are described in So, M.-K., Xu, C., Loening, A. M., Gambhir, S. S. & Rao, J. Nat. Biotechnol. 24, 339-343 (2006), the entirety of which is incorporated by reference herein.

In another embodiment, the chitosan polymer may be labeled with a radioisotope, e.g., a positron emitting radio-isotope (such as $^{31}P$, $^{11}C$, $^{18}F$ etc) for PET imaging or a gamma emitting radio isotope (such as $^{99m}Tc$, $^{111}In$, $^{123}I$ and $^{153}Sm$) for detection using gamma camera. See Perkins, A. C. and M. Frier, Radionuclide imaging in drug development. *Current Pharmaceutical Design,* 2004. 10(24): p. 2907-2921; Longjiang Zhang, Hongwei Chen, Liya Wang, Tian Liu, Julie Yeh, Guangming Lu, Lily Yang, Hui Mao; Delivery of therapeutic radioisotopes using nanoparticle platforms: potential benefit in systemic radiation therapy. *Nanotechnology, Science and Applications,* 2010, Volume 2010:3, p 159-170), the entireties of which are incorporated by reference herein.

In other embodiments, either or both of the chitosan polymer and the hydrophilic dispersing agent may be solely or additionally labeled with a target-specific ligand (target molecule), wherein the ligand has an affinity for a predetermined molecular target. Again, as with any other additional agent that may be attached to the chitosan polymer and/or the hydrophilic dispersing agent, the target-specific ligand may be attached to the chitosan polymer or the hydrophilic dispersing agent prior to combination of the first and second microemulsions. The target-specific ligand may be one or more of an aptamer, a peptide, an oligonucleotide, a folate, an antigen, an antibody, or combinations thereof. In one embodiment, the predetermined molecular target is associated with a cancer cell, a leukemia cell, an acute lymphoblastic leukemia T-cell, or combinations thereof.

In a particular embodiment, the target-specific ligand is folate, which has a known affinity for cancerous cells, such as breast cancer cells. In another embodiment, the ligand comprises an aptamer having an affinity for leukemia cells, e.g., an acute lymphoblastic leukemia T-cell. The aptamer may include any polynucleotide- or peptide-based molecule. A polynucleotidal aptamer is a DNA or RNA molecule, typically comprising several strands of nucleic acids that adopt highly specific three-dimensional conformation designed to have appropriate binding affinities and specificities towards specific target molecules, such as peptides, proteins, drugs, vitamins, or other organic and inorganic molecules. Such polynucleotidal aptamers can be selected from a vast population of random sequences through the use of systematic evolution of ligands by exponential enrichment. A peptide aptamer is typically a loop of about 10 to about 20 amino acids attached to a protein scaffold that bind to specific ligands. Peptide aptamers may be identified and isolated from combinatorial libraries, using methods such as the yeast two-hybrid system. In one embodiment, the ligand comprises the DNA aptamer sgc8c having a sequence according to SEQ. ID No. 1:

```
5'-ATC TAA CTG CTG CGC CGC CGG GAA AAT ACT GTA
CGG TTA GA-3'.
```

The DNA aptamer sgc8c has been shown to have a particular binding affinity for leukemia cells, e.g, acute lymphoblastic leukemia T-cells.

In still other embodiments, a biologically active agent may be bonded to either or both of the chitosan polymer and the hydrophilic dispersing agent. Exemplary biologically active agents include peptides (e.g., RGD peptide, integrin selective; see Dechantsreiter, M. A., et al., *N-Methylated Cyclic RGD Peptides as Highly Active and Selective $\alpha_v\beta_3$ Integrin Antagonists*. Journal of Medicinal Chemistry, 1999. 42(16): p. 3033-3040.), antibodies (e.g., CD10 monoclonal antibody for targeting human leukemia; see Santra, S., et al., *Conjugation of Biomolecules with Luminophore-Doped Silica Nanoparticles for Photostable Biomarkers*. Analytical Chemistry, 2001. 73(20): p. 4988-4993.) and proteins. The stabilized chitosan-based nanoparticies may be employed as biologic agents in that, for example, the stabilized chitosan-based nanoparticles may also be conjugated with a ligand having an affinity for a predetermined biological target so that nanoparticles are effective as target-specific probes. Likewise, either or both of the chitosan polymer and the hydrophilic dispersing agents may be conjugated with a biologically active agent, as well as with a target-specific ligand. When these two modalities are combined, the disclosed stabilized chitosan-based nanoparticies are useful as target-specific drug delivery vehicles.

The above-described methods are capable of producing stabilized, water-dispersible chitosan-based nanoparticles comprising an interconnecting network of chitosan polymer and a hydrophilic dispersing agent due to electrostatic interactions between the two components. Advantageously, the formed stabilized chitosan-based nanoparticles have an average particle size of from 20-100 nm or less, and in one embodiment, about 28 nm. In one embodiment, the stated values refer to a longest dimension of the particle. It is appreciated that larger nanoparticles may be formed however, such as 200 nm, upon agglomeration of two or more nanoparticles. Nanoparticles having a particle size of about 100 nm or less as described herein have several advantages: (i) due to large surface to volume ratio, it is possible to co-attach targeting molecules, image contrast agents and/or therapeutic drugs to the nanoparticle surface as described herein; (ii) the stabilized chitosan-based nanoparticles may be capable of evading the macrophage capture of the immune system and may remain in the circulation system for a longer time for effective therapy, (iii) intra-cellular delivery of the stabilized chitosan-based nanoparticles may be facilitated; and (iv) the stabilized chitosan-based nanoparticles may easily travel through the smallest blood capillary (5-6 microns in diameter) without forming embolism, allowing for uniform circulation.

Furthermore, the present inventors have found that the particle size of the HNPs does not typically change irrespective of whether there is provided a single-modal stabilized chitosan-based nanopaticle (such as an FITC-labeled chitosan-based pnanoparticle) or a bimodal (both FITC and Gd-DOTA labeled) stabilized chitosan-based nanoparticle. This indicates that particle size depends on microemulsion parameters, such as water to surfactant molar ratio, which may be from 2:1 to 70:1, and in a particular embodiment is about 10:1. See Padmavathy Tallury, Soumitra Kar, Suwussa Bamrungsap, Yu-Fen Huang, Weihong Tan and Swadeshmukul Santra, Chem. Commun., 2009, 2347-2349. It is appreciated that the ratio may be as much as 70:1 (or greater) in case of the AOT-based water-in-oil microemulsion systems. See Ref. De, T. K. and A. Maitra, Solution behaviour of Aerosol OT in non-polar solvents. Advances in Colloid and Interface Science, 1995. 59: p. 95-193 and reference #94 cited therein, which are incorporated by reference herein in their entirety.

In addition, in one embodiment, the stabilized chitosan-based nanoparticles have a zeta potential of at least +32 mV. Zeta ($\zeta$) potential is a parameter characterizing electric properties of interfacial layers in dispersions, emulsion, or porous bodies. The positive zeta potential of the formed nanoparticles likely indicates the presence of surface amine functional groups. The zeta potential provides information about a nanoparticle's surface charge. For example, positively charged nanoparticles may have good transfecting capability whereas negatively charged particles should have minimal or no transfecting capability. For drug delivery applications (non-targeted), it is desirable to have positively charged particle-based drug carriers.

In accordance with another aspect of the present invention, there is provided an in vivo imaging method. The method comprises administering to a subject a plurality of stabilized chitosan-based nanoparticles as in any embodiment described herein. In one embodiment, the stabilized chitosan-based nanoparticles comprise a chitosan polymer and a hydrophilic dispersing agent. In the nanoparticle, chains of the chitosan polymer electrostatically interact with chains of the hydrophilic dispersing agent to form an entangled network comprising the chitosan polymer and the hydrophilic dispersing agent. In one embodiment, the stabilized chitosan-based nanoparticles have an average particle size of about 100 nm or less. In addition, the method further comprises detecting a presence of the stabilized chitosan-based nanoparticles.

The administering may be done according to any suitable route of in vivo administration that is suitable for delivering the composition into a patient (e.g., human or animal subject). The preferred routes of administration will be apparent to those of skill in the art, depending on the medium and/or the predetermined molecular target. Exemplary methods of in vivo administration include, but are not limited to, intravenous administration, intraperitoneal administration, intramuscular administration, intranodal administration, intracoronary administration, intraarterial administration (e.g., into a carotid artery), subcutaneous administration, transdermal delivery, intratracheal administration, intraarticular administration, intraventricular administration, inhalation (e.g., aerosol), intracranial, intraspinal, intraocular, intranasal, oral, bronchial, rectal, topical, vaginal, urethral, pulmonary administration, impregnation of a catheter, direct injection into a tissue, or combinations thereof. The detecting may be done by any suitable detection method known in the art appropriate for the particular type of imaging agent incorporated into the stabilized chitosan-based nanoparticles. For in vivo detection/imaging, suitable imaging techniques such as magnetic resonance imaging (MRI), positron emission tomography (PET), X-ray computed tomography (CT scan), X-ray, fluorescence-based imaging, and the like may be used.

In one embodiment, the imaging agent for the method comprises a fluorophore, a paramagnetic chelate having a paramagnetic ion bound therein, or both. In addition, the stabilized chtiosan-based nanoparticles may further include a target-specific ligand and/or a biologically active agent bonded to the either or both of the chitosan polymer and the hydrophilic dispersing agent, wherein the ligand is specific for a predetermined molecular target.

The following examples are intended for the purpose of illustration of the present invention. However, the scope of the present invention should be defined as the claims appended hereto, and the following examples should not be construed as in any way limiting the scope of the present invention.

Example 1

1.1 Materials

Chitosan polymer (CS) (60-190 kDa), PGA (M.W. 4130 Da), Triton X-100 (TX-100), N-hydroxysuccinimide (NHS), 1-ethyl-3-(3-dimethylaminopropyl carbodiimide hydrochloride) (EDC) were purchased from Sigma-Aldrich Chemical Co., USA. Fluorescein isothiocyanate (FITC), folic acid, lysozyme enzyme and anhydrous ethanol were purchased from Fisher Scientific, USA. Dialysis membrane (MW cut off, 6-8 kD) was purchased from Spectrum Laboratories (Rancho Dominguez, Calif.). Membrane based 0.22 micron syringe filters were purchased from Millipore, USA. All other solvents and reagents were obtained from Fisher Scientific, USA and were used without any further purification.

It is noted that as used below, HNPs (stabilized chitosan-based nanoparticles) may refer to stabilized chtiosan-based nanoparticles comprising chitosan and a hydrophilic dispersing agent, e.g., PGA, as described above, wherein the chains of the chitosan polymer electrostatically interact with chains of the hydrophilic dispersing agent. The term "HNPs" may refer to such nanoparticles with or without a cross-linking compound; however, the term HNPs is generally used to refer to non cross-linked nanoparticles as the present inventors have found that non cross-linked particles provide advantages suitable for in vivo usage, such as greater biodegradability. Similarly, as noted above, the terms "chitosan nanoparticles," "CS NPs," or "CS nanoparticles" are intended to be used interchangeably and refer to chitosan nanoparticles without a hydrophilic dispersing agent as described herein. These nanoparticles include a cross-linker, typically tartaric acid.

1.2 Fluorescent Labeling of CS Polymer

Fluorescent labeling of CS polymer was done by reacting with fluorescein isothiocyanate (FITC, an amine-reactive fluorescent dye). See M. Huang, E. Khor and L.-Y. Lim, *Pharmaceutical Research*, 2004, 21, 344-353. Briefly, about 6 mL of about 0.25% CS solution in about 1% acetic acid was mixed with equal volume of anhydrous ethanol. About 10 mg of FITC was dissolved in about 2 mL of anhydrous ethanol followed by purging with nitrogen gas for about 5 minutes. The FITC solution was then added to the CS solution and the mixture was stirred overnight in the dark. Next, the pH of the solution was raised to about 9.0 using dilute NaOH that resulted in precipitation of FITC-labeled CS polymer. To remove any unbound FITC, the precipitate was repeatedly washed (roughly 4-5 times) with an ethanol:water mixture (about 70:30 V/V) and centrifugation was used to collect precipitate during washing process. The precipitate was then redispersed in about 6 mL of about 1% acetic acid solution, dialyzed against DI water for about 24 hours using a Spectra/Por molecular porous membrane, and then finally passed through an about 0.2 micron filter. The filtrate containing FITC-labeled CS polymer was checked for the FITC fluorescence and was finally used for HNP synthesis.

1.3 Folate Conjugation

Attachment of folate to polymer (CS and PGA) was done using water-soluble carbodiimide coupling chemistry that forms stable amide bonds.

1.3.1 Synthesis of PGA-Folate Conjugate

About 2.2 mg of EDC was mixed with about 5 mL of about 0.1% PGA polymer solution in DI water for about 30 min followed by addition of about 3.2 mg of folate in about 1 mL of dimethyl sulfoxide (DMSO). The mixture was magnetically stirred overnight in the dark. Next, the solution was centrifuged and the PGA-folate precipitate thus obtained was twice washed with de-ionized (DI) water (2 times) and then with a DMSO and water mixture (about 1:1 V/V). The final precipitate was re-suspended in DI water and dialyzed for approximately two days using a Spectra/Por molecular porous membrane. After about 2 days of dialysis, the solution was centrifuged at about 7500 rpm for about 15 min to remove any large aggregates and then passed through the approximately 0.2 micron filter. In this conjugation reaction, the amine groups of folate reacted with the carboxyl groups of PGA. The fluorescence spectra of the filtrate were finally taken to confirm the presence of folate and to ensure that not all the PGA-folate goes through the dialysis membrane.

1.3.2. Synthesis of CS-Folate Conjugate

Folate conjugation with CS polymer was done as described below. Activation of folate was done by adding about 2.2 mg of EDC to about 3.2 mg of folic acid in about 1 mL of DMSO and stirring was continued for about 30 min. Then, about 6 mL of CS polymer solution (about 0.25% in about 1% acetic acid) was added and the reaction was continued for overnight under dark conditions. The pH of the solution was raised to about 9.0 to precipitate folate-CS conjugate. The precipitate was washed approximately 2 times with DI water and approximately 2 times with water/DMSO mixture (about 1:1 V/V). The precipitate was then dispersed in about 6 mL of about 1% acetic acid solution and dialyzed for about 2 days using a Spectra/Por molecular porous membrane. The dialyzed solution was centrifuged at about 7500 rpm for about 15 min and then passed through the approximately 0.2 micron filter. The fluorescence spectra were taken for the presence of folate. In this conjugation reaction amine group of CS reacted with carboxyl group of folic acid.

1.3.3 Synthesis of CS-PGA HNPs

A plurality of different hybrid nanoparticles comprising chitosan polymer and PGA were synthesized using an aqueous phase/oil/surfactant (e.g., TritonX-100/cyclohexane/n- hexanol/water) in W/O microemulsion system as described in P. Tallury, S. Kar, S. Bamrungsap, Y. F. Huang, W. H. T and S. Santra, *Chemical Communications*, 2009, 2347-2349, the entirety of which is incorporated by reference. The water to surfactant molar ratio was kept constant at about 10:1. Briefly, two and/or three separate microemulsions were prepared, one for CS polymer (ME 1), one for PGA polymer (ME II) and one for the cross-linker (ME III) (See FIG. 1). The microemulsions were the same with the exception of the aqueous phase, which may included CS, PGA, or the cross-linker. A typical W/O ternary microemulsion system comprises cyclohexane (11.0 mL), n-hexanol (4.0 mL), water (total volume of aqueous phase, 4.0 mL) and TX-100 (neat, as received from Sigma-Aldrich; 6.0 mL). Water to TX-100 surfactant molar ratio was 22:1.

Four different molar ratio of PGA:CS, about 1:20, about 1:10, about 1:5 and about 1:1 were used for HNP synthesis and the ratio with best buffer stability (about 1:10) was used for further studies. The tartaric acid cross-linker used for making covalently cross-linked HNPs was activated by carbodiimide coupling agent, EDC, where tartaric acid, EDC and NHS were combined in a ratio of about 1:5:2 in about 4 mL DI water and reacted for about 15 minutes. Microemulsion I (ME I) was stirred for at least 1 hour and microemulsion II (ME II) was stirred for at least 30 min before ME II was added drop wise to ME I under constant stirring. ME III wherever applicable was added about 2-3 hrs after addition of ME II to ME I, to allow mixing of two microemulsions (ME I and ME II). In both the cases, the reaction was allowed to continue under dark conditions for about 24 hrs at room temperature. The nanoparticles were then collected by destabilizing the microemulsion by adding ethanol followed by centrifugation. The yellow colored nanoparticles were washed repeatedly (about 4-5 times) with ethanol to remove surfactant and other unreacted materials. Sonication and vortexing techniques were used for re-dispersing particles in washing solution. Finally, about 3 mL of DI water was added to the washed nanoparticles and the solution was freeze-dried to obtain nanoparticles in dry powder form.

Six different nanoparticles varying in cross-linking and/or the conjugation of folic acid to the polymer were synthesized for a PGA:CS molar ratio of about 1:10 (optimal ratio as concluded below). The six different nanoparticles were as follows:

CS-A: In this nanoparticle, the CS polymer was FITC labeled and folate conjugated. The polymer was cross-linked with tartaric acid.

CS-B: These were the HNPs in which tartaric acid was replaced by PGA. The CS polymer was labeled with FITC whereas the folate was conjugated to PGA. The synthesis procedure was the same as CS-A except that CS and PGA polymer chains were electrostatically stabilized and no covalent cross-linking process was involved.

CS-C: These particles were same as the CS-B, the only difference in folate being conjugated to CS polymer.

CS-D: These HNPs were formed by cross-linking CS-PGA complex with tartaric acid. CS polymer was separately labeled with FITC and folate. Three different microemulsions were used as shown in FIG. 1.

CS-E: These nanoparticles were cross-linked with tartaric acid as in CS-D. CS polymer was FITC-labeled whereas folate was conjugated to PGA polymer.

CS-F: These CS-PGA HNPs were used as controls for cell culture studies and these HNPs did not contain folate.

1.4 Nanoparticle Characterization

Particle size distribution and hydrodynamic diameter of particles in DI water (about pH 6.5) and in PBS were measured using a Precision Detector PD2000 DLS plus instrument. Transmission Electron Microscopy (TEM) was used for the size measurement of nanoparticles in the dry state. Samples for TEM were prepared by placing a drop of particles on carbon coated grids (about 400 mesh size) followed by air drying. Images were taken on a JEOL 1011 Transmission Electron Microscope. Zeta potential ($\zeta$) measurements of HNPs in DI water were done on a Zetasizer Nano ZS instrument (Malvern Instruments Ltd.) to characterize surface charge of the polymers and nanoparticles. The reported $\zeta$ value was the average of five measurements. Transmittance of HNPs solution (concentration of about 1 mg/mL) was measured at room temperature using a Cary 300 Bio UV-Vis spectrophotometer. Quartz cuvettes were used for transmittance measurements. The fluorescence emission and excitation spectra of HNPs loaded with FITC and/or folate were recorded on a Nanolog spectrofluorometer (Horiba Jobin-Yvon Nanolog).

1.5 Nanoparticle Degradation Studies

A comparative enzymatic degradation study was done for the assessment of degradability of cross-linked and non cross-linked nanoparticles using lysozyme solution. L. Kong, Y. Gao, G. Lu, Y. Gong, N. Zhao and X. Zhang, *European Polymer Journal*, 2006, 42, 3171-3179. The HNPs and the CS NP (control) were immersed in 4 mg/mL lysozyme solution and incubated at about 37° C. under continuous shaking. The ratio of the particle weight to the lysozyme solution volume was about 2 mg/mL. The lysozyme solution was replaced with fresh solution every week. The readings of residual particle mass were taken at a regular interval. A typical procedure involved removal of degraded soluble part by centrifugation followed by freeze drying and weighing. In vitro degradation was expressed as the percentage of the dried weight of nanoparticles after lysozyme treatment.

1.7 In Vitro Studies

Receptor-mediated nanoparticle uptake was studied using folate receptor over-expressing cancer cells, MDA-MB-231 cells (human breast cancer cell line, American Type Culture Collection, Rockville, Md.) and TE-71 (thymic epithelial cell line, American Type Culture Collection, Rockville, Md.; a control cell line). Cells were grown in Dulbecco's modified Eagle's medium (DMEM) containing about 10% heat-inactivated fetal bovine serum, antibiotic-penstrep penicillin, and streptomycin mixture (Invitrogen, Inc., USA). Cells were cultured in a 12-well plate (Cellstar, Greiner Bio-One North America Inc., Monroe, N.C., USA) for about 24 hours to allow cells to adhere to the surface of glass slides that were placed in the well (Fisher Scientific, Pittsburgh, Pa., USA) and begin logarithmic growth. Cells at ~50% confluence were incubated with the nanoparticles formed above. In a typical procedure, cell medium was removed from the well plate followed by addition of new cell medium containing nanoparticles. Each nanoparticle solution in cell medium was prepared by mixing about 50 µl of about 10 µg/ml nanoparticle solution with phosphate-buffered saline (PBS buffer) 0.95 ml cell medium. The treatment was done for about 5 hours in a humidified cell culture incubator containing about 5% $CO_2$ at about 37° C. Prior to fluorescence imaging, the medium was removed and the cells were thoroughly washed six times with PBS buffer to remove unbound nanoparticles. Subsequently, fluorescence images were recorded under a Zeiss Axiovert 200 fluorescent microscope and images were processed using the AxioVision E 4.8 software.

2.1 Particle Formation and Buffer Stability (Results)

Hybrid (stabilized chitosan-based) nanoparticles were synthesized using W/O microemulsion method via electrostatic interaction between chitosan polymer and PGA polymer. The compartmentalization of CS and PGA polymer chains occurred within the confined environment of microemulsion water droplet. The mixing of different microemulsions ensures the uniform distribution of polymers and controlled particle formation within the microemulsion droplet. At neutral or basic pH conditions, CS polymer stays in globular form (collapsed state) due to the weakly basic ($pK_a$=6.2-7) property of CS polymer. In acidic conditions, however, the CS polymer is highly charged due to protonation of amino sugar moieties and because of this high charge density polymer expands in acidic condition ("swelled state"). Since PGA, on the other hand, is a weak acid, the carboxyl groups of PGA ($pK_a$~5.0) remain deprotonated at neutral or basic pH conditions. When two such oppositely charged polymers are mixed, they self assemble to form complex network structures due to electrostatic interactions, without the use of any cross-linker. Thus, in this case, it is believed that the positively charged CS polymer will electrostatically entangle with negatively charged PGA once they are combined in aqueous solution, thus forming HNPs.

Figure 2:
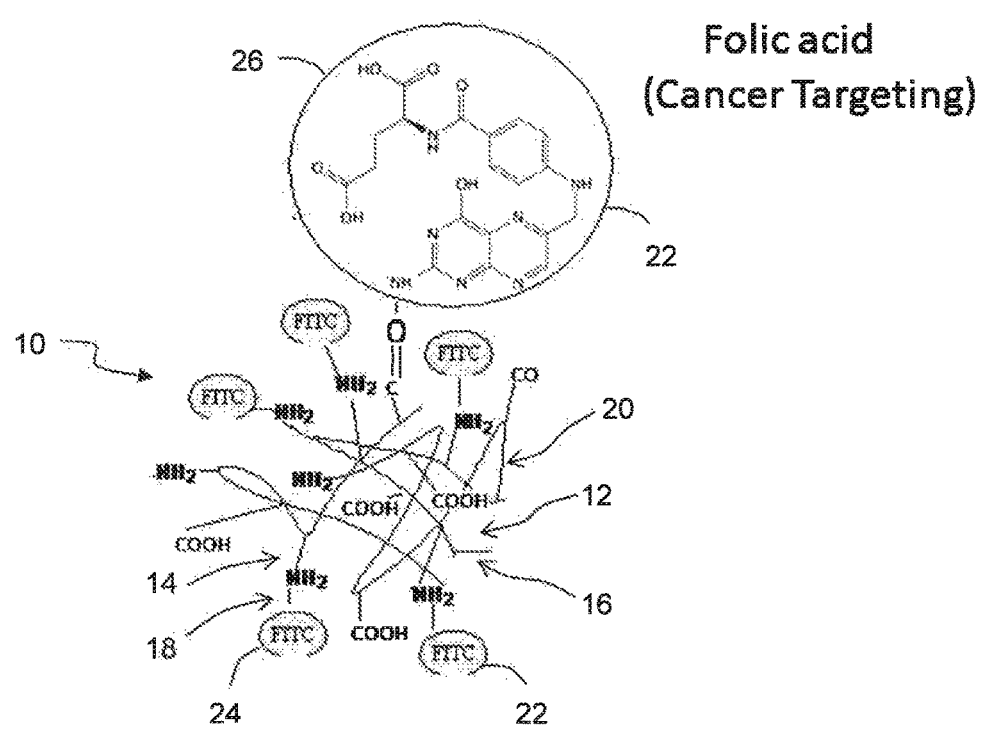
FIG. 2 is a representative particle construct for chitosan-based hybrid nanoparticles (HNPs) showing the electrostatic entanglement of the two polymers (chitosan and PGA) and their conjugation with FITC and folic acid.

Referring to FIG. 2, there is shown an exemplary stabilized chitosan-based nanoparticle 10. The nanoparticle 10 comprises a chitosan polymer 12 and a hydrophilic dispersing agent 14. As shown, chains 16 of the chitosan polymer 12 electrostatically interact with chains 18 of the hydrophilic dispersing agent 14 (e.g., PGA) to form an entangled network 20 comprising the chitosan polymer 12 and the hydrophilic dispersing agent 14. In the illustrated embodiment, there are a pair of ligands 22 attached to the polymeric chains 12, 14. The ligands 22 comprise an imaging agent 24 (e.g., FITC) and a target specific ligand 26 (e.g., folic acid), though it is understood the ligands may be or further comprise any other ligands as described herein.

It is appreciated that the formation and stability of such a complex (entangled network) is determined by various factors such as concentration of polymers, molecular weight of polymers, degree of ionization, charge density of polymers, charge distribution over the polymeric chains, and the ratio of the two polymers.

It is believed that PGA not only facilitates the formation of HNPs via electrostatic entanglement and maintains the particle integrity, but also increases overall stability of nanoparticles. The particle integrity is maintained by better entanglement or cross-linking of the two polymers. The size and stability of the HNPs was found to be dependent on PGA:CS ratio (see Table 1 below). It is noted that the nanoparticles of Table 1 were unlabeled, meaning the nanoparticles were formed as described above, but were not conjugated with an imaging agent (e.g., FITC) or folate.

TABLE 1

Compiled summary of CS-PGA HNPs at different ratios of PGA:CS.

| PGA:CS ratio | DLS size in water (nm) | DLS size in PBS (nm) | TEM size (nm) | Transmittance at 500 nm (%) | Zeta potential (mV) |
|---|---|---|---|---|---|
| 1:20 | 120 | 242 | ~60 | 66.61 | +37.8 |
| 1:10 | 57 | 63 | ~28 | 99 | +32.6 |
| 1:5 | 102 | 219 | ~50 | 62.18 | +26.3 |
| 1:1 | 133 | 312 | ~80 | 3.86 | +16.4 |

As shown, the optimal molar ratio of PGA to CS was found to be about 1:10 to achieve the best stability and integrity in DI water, and also in PBS solution at about pH 7.4 without increasing particle size. The poor stability of chitosan-based nanoparticles (without a hydrophilic dispersing agent) (CS NPs) in PBS can be attributed to particle agglomeration due to passivation of surface charges. In the case of HNPs, it appears that PGA disrupts particle-particle interaction, preventing particle agglomeration.

At higher and lower PGA:CS ratios than about 1:10, the nanoparticles were more unstable and tended to precipitate out a bit more giving a turbid solution. At higher ratios of PGA:CS, the two charges balance each other such that the net charge is either zero or too little for particles to be stable in the solution. In general, if the ratio of two polymers is such that one charge is in excess, the complex formed is non-stoichiometric and is soluble, whereas a stoichiometric complex with net zero charges is usually insoluble and precipitates out. At a very low ratio of PGA:CS, the amount of PGA present is not enough to interact with chitosan polymer and form nanoparticle, thus compromising the integrity and stability of the particle.

At appropriate ratio of the two polymers, the electrostatic entanglement/cross-linking of the two polymers maintains the chitosan-based nanoparticle integrity, hence, obviating the need of covalent cross-linker for the synthesis. This may further result in improved biodegradability of non cross-linked HNPs over cross-linked HNPs. In case of cross-linked HNPs, additional parameters, such as the concentration and hydrophilicity of the cross-linkers may determine particle stability.

3.1 Characterization of HNPs

3.1.1 Zeta Potential Measurements

The $\zeta$ values of CS and PGA polymers were about +60.8 mV and about −58.3 mV, respectively, reflecting the presence of positively charged amine groups with CS and negatively charged carboxyl groups with PGA polymers. The net charge on the particles HNPs varied with PGA:CS molar ratio. Table 1 (above) summarizes the $\zeta$ values for HNPs at different PGA:CS molar ratios. It is clearly seen that the net charge on HNPs decreases with increase in PGA:CS molar ratio. Table 2 below compiles data obtained from zeta potential measurements for different cross-linked and non cross-linked nanoparticles at 1:10 ratio of PGA:CS. The $\zeta$ value of CS nanoparticles was about +44.8 mV. The $\zeta$ value decreases to about +32.6 mV in HNPs (stabilized chitosan-based nanoparticles). This reduction in $\zeta$ value is due to electrostatic interaction of PGA with CS polymer. The $\zeta$ value of tartaric acid cross-linked HNPs was about +23.6 mV (Table 2). In addition to electrostatic interaction between CS polymer and PGA, consumption of amine groups of CS during cross-linking with tartaric acid further decreases the surface charge of cross-linked HNPs.

solubility of CS particles, but it also consumes some of the amine groups, during cross-linking process. Hence, moder-

TABLE 2

Compiled summary of CS-PGA HNP and cross-linked CS NP synthesis strategy,
TEM and DLS data for particle size and zeta potential values.

| Sample | M. E. I | M. E. II | M. E. III | Type of interaction | DLS size in water (nm) | DLS size in PBS (nm) | TEM size (nm) | Transmittance at 500 nm (%) | Zeta potential (mV) |
|---|---|---|---|---|---|---|---|---|---|
| CS-A | CS, CS-folate and CS-FITC | Tartaric acid, EDC, NHS and DI water | — | Covalent cross-linking | 78.2 | 277 | ~28 | 53 | +44.8 |
| CS-B | CS, CS-FITC | PGA-folate | — | Electrostatic interaction (no cross-linker) | 57 | 63 | ~28 | 99 | +32.6 |
| CS-C | CS-folate and CS-FITC | PGA | — | Electrostatic interaction (no cross-linker) | 61.2 | 64 | ~28 | 99 | +33.4 |
| CS-D | CS-folate and CS-FITC | PGA | Tartaric acid, EDC, NHS and DI water | Electrostatic interaction followed by covalent cross-linking | 144 | 237 | ~60 | 38 | +23.6 |
| CS-E | CS-FITC | PGA-folate | Tartaric acid, EDC, NHS and DI water | Electrostatic interaction followed by covalent cross-linking | 198 | 306 | ~60 | 38 | +24.3 |
| CS-F | CS-FITC | PGA | | Electrostatic interaction (no cross-linker) | 64.1 | 65 | ~28 | 99 | +34.7 |

3.1.2 Light Scattering Measurements

Figure 4A:
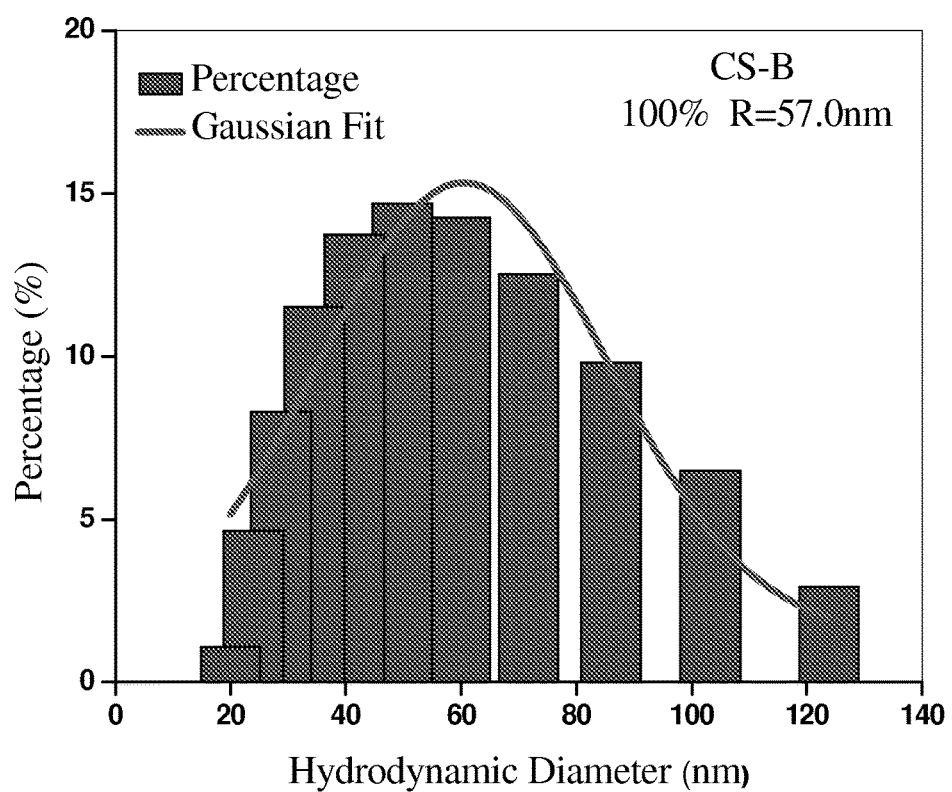
FIG. 4A-4D show particle size distribution profiles obtained from DLS measurements, specifically: (a) chitosan (CS) nanoparticles in DI water (fairly monodispersed); (b) CS nanoparticles in PBS (highly polydispersed); (c) non cross-linked hybrid nanoparticles (HNPs) in DI water (fairly monodispersed) and (d) non cross-linked hybrid nanoparticles (HNPs) in PBS, pH 7.4 (fairly monodispersed).
Figure 4B:
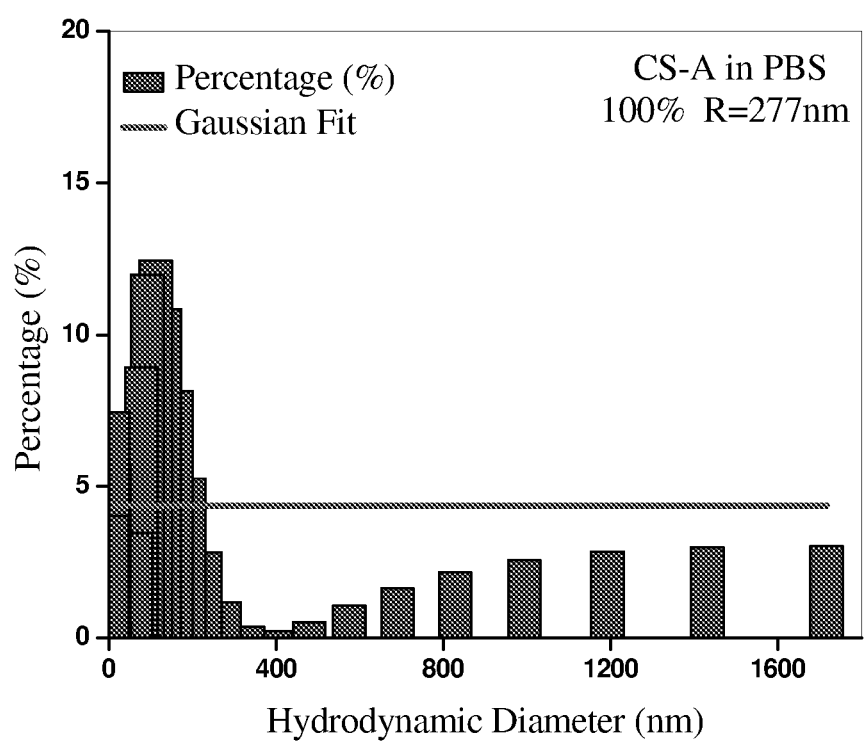
Figure 4C:
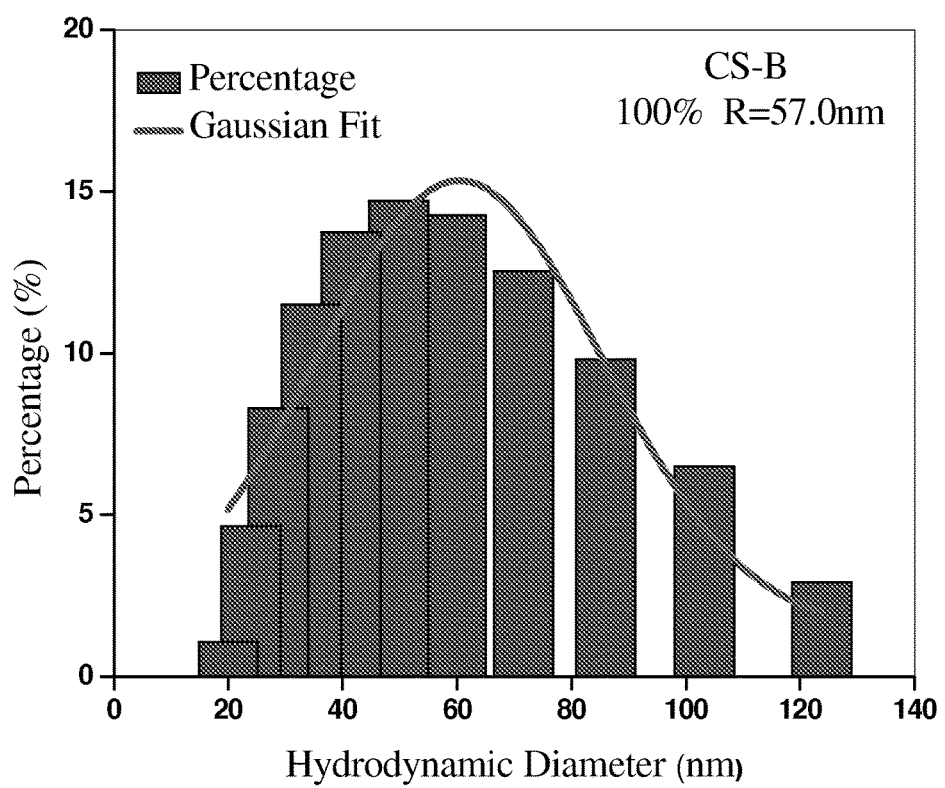
Figure 4D:
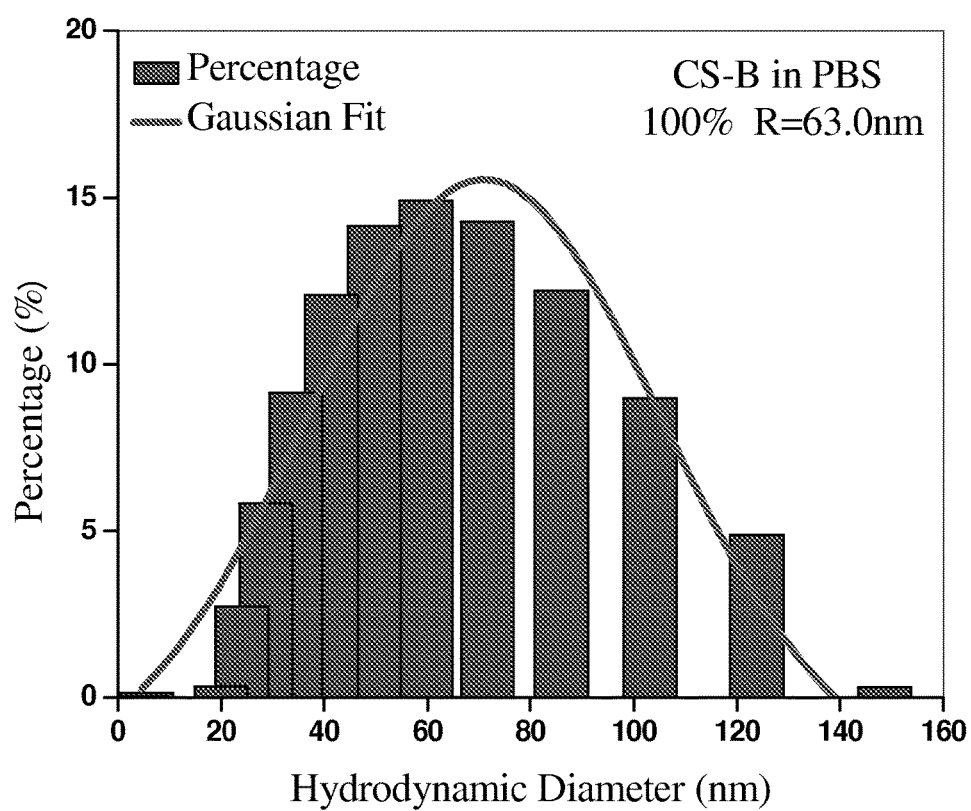

Buffer is a preferred medium for dispersing nanoparticles for most biological experiments. It is therefore desirable and realistic to measure hydrodynamic diameter and particle size distribution in PBS at about pH 7.4.

a) Effect of PGA:CS ratio on the stability of HNPs. FIGS. 3A-3H show DLS data for HNPs for different PGA:CS ratio in DI water and PBS (pH 7.4). It is evident from the data that a molar ratio of about 1:10 gives the best result. The particles are stable in PBS and give a size distribution similar to that in DI water. At higher and lower ratios of PGA to CS, the particle size is higher than that of 1:10 in DI water and particle stability is compromised. At 1:10, the particles are stable for months at room temperature.

b) Effect of cross linking on stability of HNPs: The DLS data clearly demonstrates improvement in stability of HNPs in PBS over tartaric acid cross-linked CS NPs (FIG. 4A). Cross-linked CS NPs are stable in water; however, their stability is compromised in PBS, resulting in agglomeration (FIG. 4B). HNPs were shown to be highly stable both in DI water and in PBS buffer at about pH 7.4 (FIG. 4C and FIG. 4D).

Referring to FIGS. 5A-5F, FIGS. 5A-5F show the hydrodynamic diameters of each of the six different particles (CS-A through CS-F). As shown, the non cross-linked nanoparticles are more uniform in size than cross-linked nanoparticles.

Figure 5A:
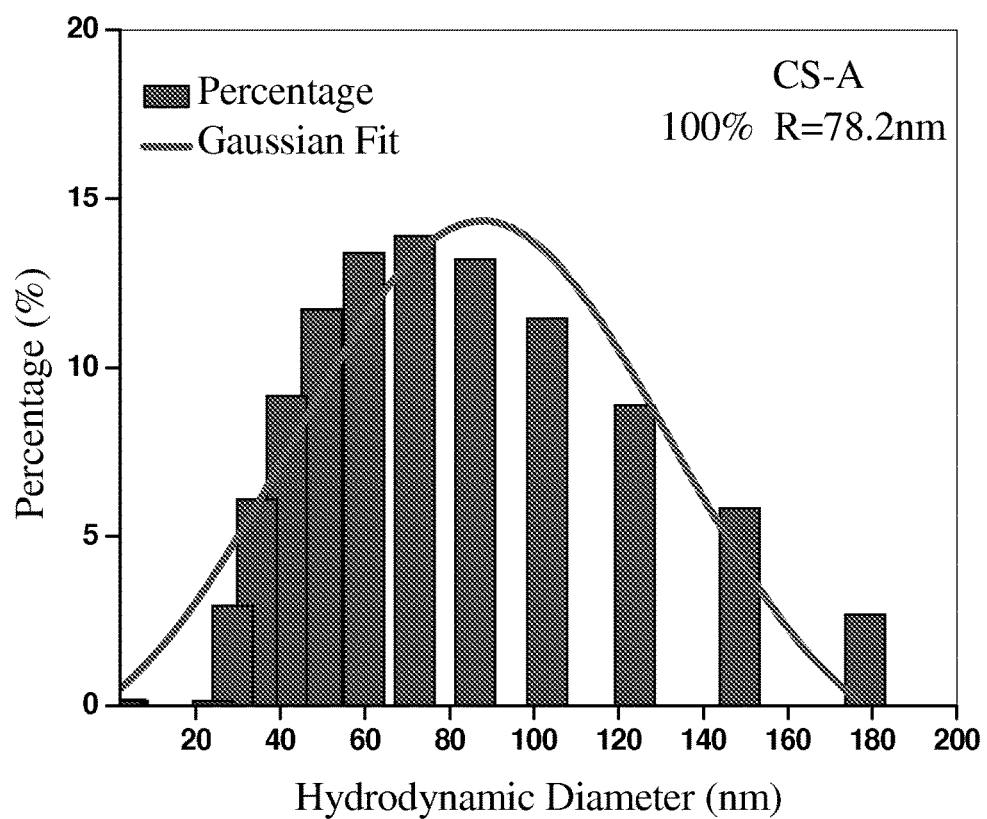
FIGS. 5A-F represent DLS data showing hydrodynamic diameter for all the nanoparticles (NPs) synthesized (CS-A to CS-F).
Figure 5B:
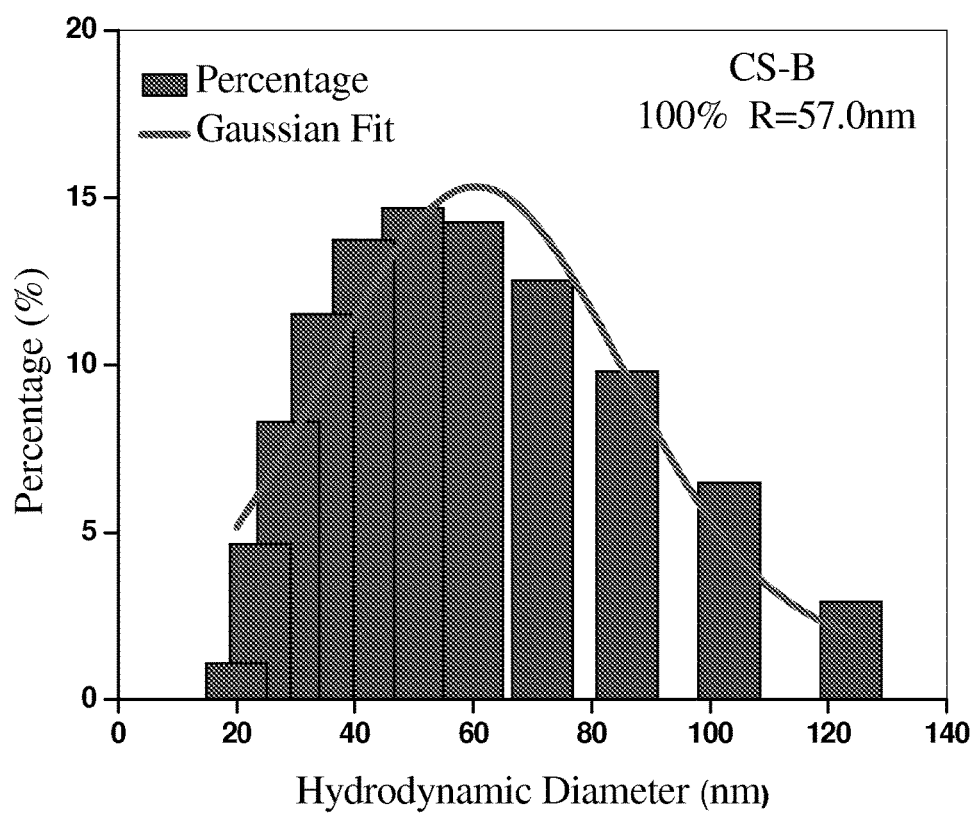
Figure 5C:
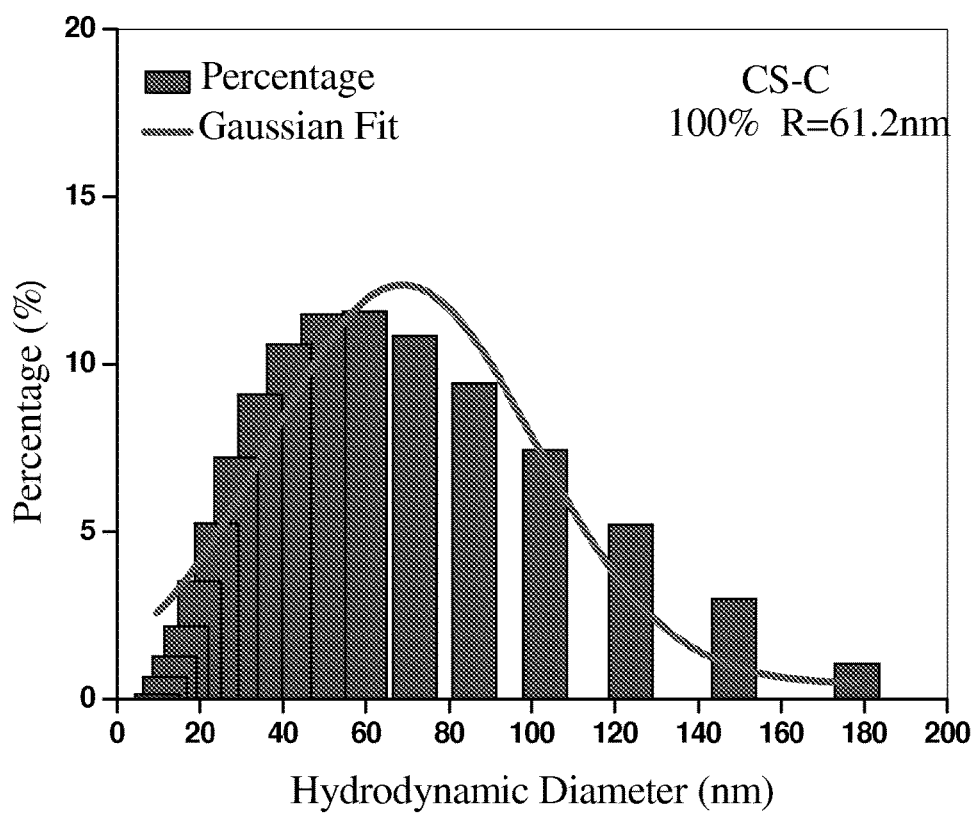
Figure 5D:
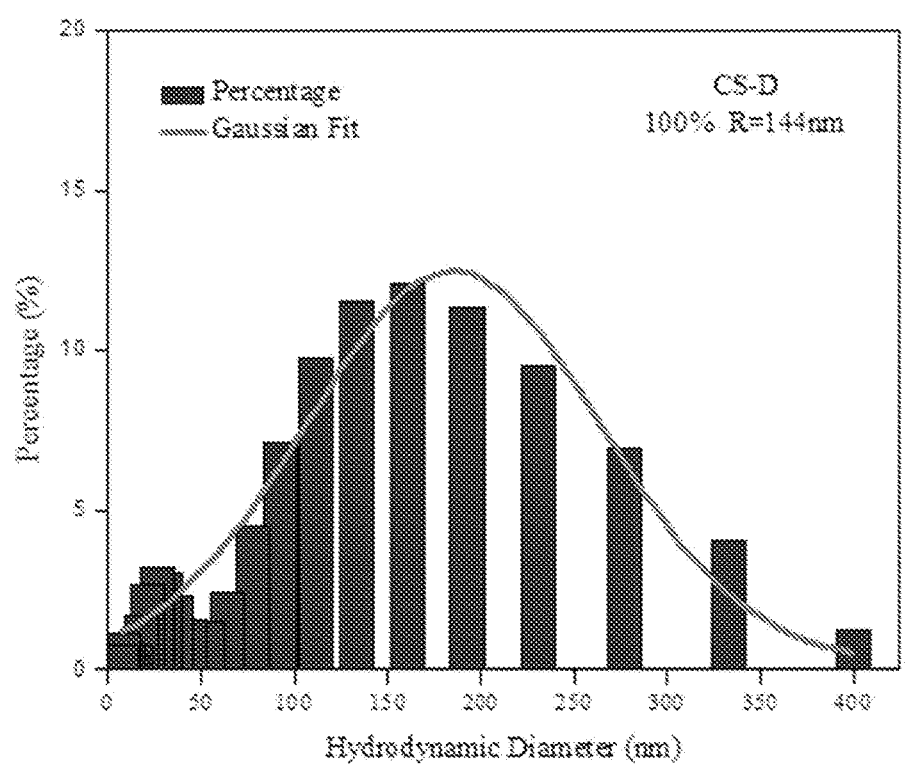
Figure 5E:
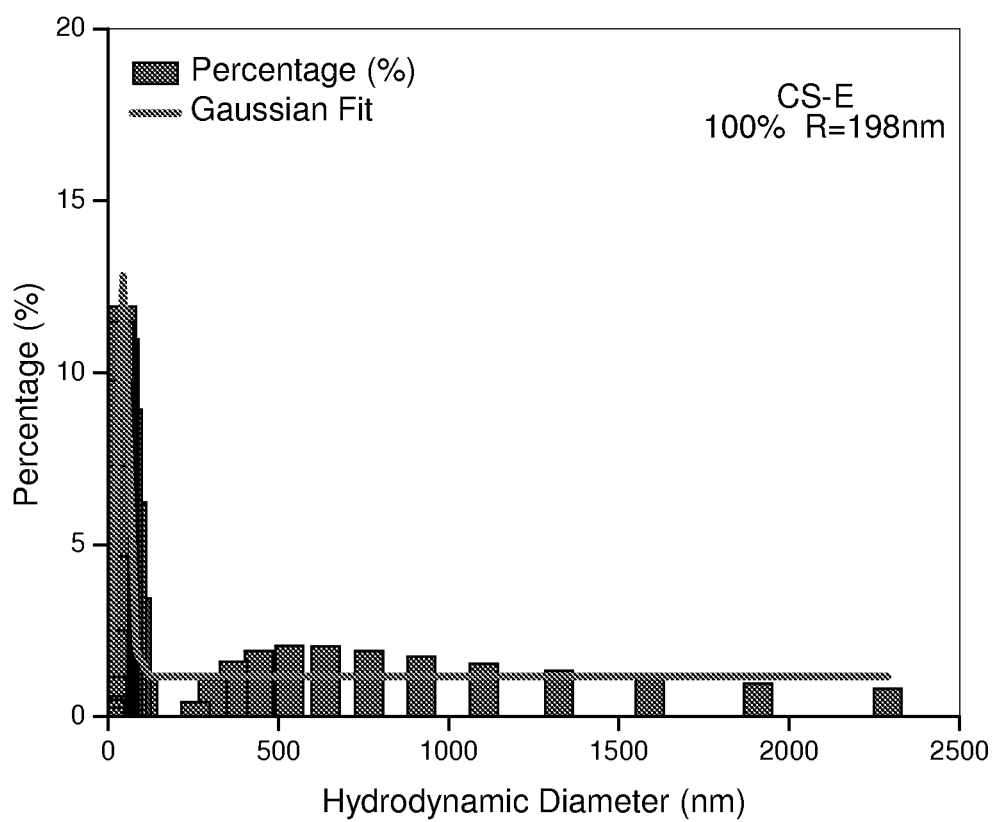
Figure 5F:
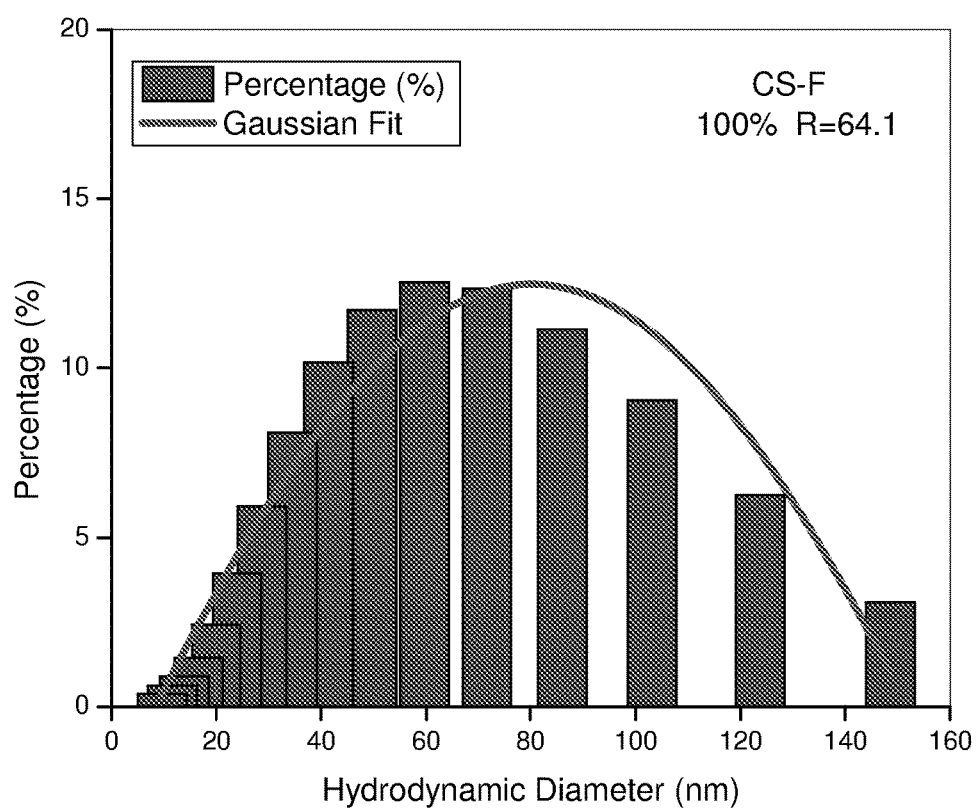

In sample CS-A, tartaric acid was used as a cross-linker. Since tartaric acid is hydrophilic in nature, it enhances the ate stability was observed (FIG. 5A). Sample CS-B and CS-C are more hydrophilic due to the presence of PGA which creates additional hydrophilic domains and reduces high surface energy, thus improving stability. Electrostatic interaction between PGA and CS chains in HNPs provides significant particle integrity and overall stability (FIGS. 5B-5C). The minor difference in the particle size distribution of CS-B and CS-C can be attributed to a significant reduction in number of free amines on chitosan (in CS-C) because of folate conjugation along with FITC on the chitosan polymer. In samples CS-D and CS-E, further cross-linking of the HNPs were done with tartaric acid (FIGS. 5D-5E). This covalent cross-linking process replaced highly hydrophilic amines and carboxyl groups with less hydrophilic hydroxyl groups and decreased overall surface charge. As a result, the stability of cross-linked HNPs particle was compromised in comparison to non cross-linked HNPs.

3.1.3 Transmittance Measurements

The stability of the nanoparticles was also evaluated by transmittance (or turbidity) measurements at pH 7.4. Table 1 (above) summarizes the transmittance value of the nanoparticles at different PGA:CS ratios. Based on the data, it can be concluded that at about a 1:10 PGA:CS ratio, the HNPs at stable with a transparent solution (about 99% transmittance), whereas at very low or high concentration the solutions are relatively more turbid with maximum turbidity at about 1:1 (FIG. 6) (1:20, 1:10, 1:5, and 1:1 left to right). Similarly lower transmittance of cross-linked chitosan (no hydrophilic dispersing agent) nanoparticles (CS NPs) (about 53%) and cross-linked HNPs (about 38%) confirmed that cross-linking increases the turbidity (i.e. decreases stability). As expected, electrostatically entangled HNPs had about 99% transmittance, confirming excellent stability (Table 2). All these results are in perfect agreement with DLS results.

3.1.4 Particle Size Characterization

Polymeric particles such as CS NPs (chitosan only nanoparticles) and HNPs (chitosan and PGA) are considered soft particles. TEM of particles was done under vacuum conditions; hence TEM image would reflect physical size in the dry state. It was therefore expected that the estimated particle size from TEM imaged would be lower than that measured in solution. As expected, it was observed that DLS estimated particle size was larger than that estimated by the TEM. Moreover, TEM showed a narrower particle size distribution in comparison to that observed in DLS. The water pool of the W/O microemulsion system provides a constrained environment that facilitates the formation of monodispersed particles and minimizes undesirable particle agglomeration.

FIGS. 7A-7D show TEM images of HNPs with different PGA:CS ratios. The effect of PGA:CS ratio on particle size and morphology is evident from the images. For a ratio of about 1:20, the particles are bigger with no specific shape; it seems as if the particle integrity is compromised because of poor entanglement of the two polymers due to low concentration of PGA. Average particle size for particles having a molar ratio of about 1:10 PGA to CS is approximately 28 nm with fair monodispersity, and particles are spherical in shape. At a molar ratio of about 1:5, the particle size distribution is broad consisting of a mixture of small and big particles, the average size somewhere around 50 nm (Table 1). The particle shape distribution is also bimodal with some spherical and some elongated particles. At a molar ratio of about 1:1, the particle size is much bigger (80 nm) than for the about 1:10 and again bimodal shape distribution is observed. From the images above, it can be concluded that the about 1:10 gives small, monodispersed particles.

TEM images for CS NPs and non cross-linked and cross-linked HNPs with about a 1:10 PGA:CS molar ratio are shown in FIGS. 8A-C. TEM images of synthesized CS NPs and HNPs demonstrated formation of fairly monodispersed particles with a uniform size distribution. An average particle size was estimated to be about 28 nm. Some particles in the TEM image appeared to be of bigger size. A careful investigation, however, reflects that these are particle clusters composed of a few particles. The formation of such particle clusters could be attributed to the mucoadhesive nature of CS polymer. The TEM image of cross-linked particles shows a mixture of small and big particles with spherical and non-spherical shapes. These features may be because of further inter-particle cross-linking by the cross-linker.

3.1.5 Fluorescence Excitation and Emission Spectra

Fluorescence excitation and emission spectra were recorded for FITC and folate-labeled particles. Multiple emission peaks were observed due to presence of both FITC and folate chromophores within the same particle. Spectral characteristics of FITC (excitation and emission band maxima, 490 nm and 519 nm, respectively, FIG. 9A) did not change upon tagging with particles. These results suggest that particles are well hydrated and the aqueous microenvironment around FITC is similar to bulk water. The folate conjugated NPs showed characteristic dual emission at 355 nm and 440 nm when excited at 280 nm (FIG. 9B) and the excitation spectra recorded at 440 nm emission, gives two characteristic excitation peaks at 280 nm and 355 nm (FIG. 9C). The characteristic excitation and emission peaks of FITC and folate confirm their presence in HNPs. Confocal image of HNPs deposited on a microscope slides showed bright green fluorescence characteristic to FITC emission, indicating suitability of these particles for in vitro studies using cell cultures.

3.1.6 Biodegradation Studies

Enzymatic biodegradation studies were carried out using lysozyme, which is the main enzyme that degrades chitosan (CS) in the body. The biodegradability of CS and related materials are generally investigated using a lysozyme solution. The degradation rate was evaluated on the basis of weight loss after the enzymatic hydrolysis. No noticeable degradation of cross-linked CS particles was observed over the first week, but HNPs showed some degradation as shown in FIG. 10. Significant degradation of non cross-linked HNPs was noticed from second week. As expected, the non-cross-linked HNPs degraded several times faster than CS NPs and the cross-linked HNPs. The degradation rate of cross-linked HNPs was similar to CS NPs for almost three weeks. However, after the completion of third week, the former degraded at faster rate than the later. This study confirmed that covalent cross-linking slowed down degradation of CS nanoparticles and cross-linked HNPs. The presence of PGA in HNPs not only improves their stability but also accelerates biodegradation. This faster degradation is another advantage of HNPs for biomedical applications.

3.1.7 Cell Culture Studies

To demonstrate the applicability of HNPs for imaging cancer cells, HNPs were targeted to human breast cancer cell line MDA-MB 231, which over express folate receptors. The thymus cell line (TE-71) was used as control cell line, as it is a non-cancerous cell line and does not over express folate receptors. NPs without folate (CS-F) were used as control to rule out any possibility of non-specific binding to MDA-MB 231 cells. Confocal images of HNPs treated MDA-MB 231 cells and TE-71 cells were shown in FIGS. 11A-B respectively. As expected, no significant uptake of folate conjugated particles by the TE-71 cells was observed, suggesting normal expression of folate receptors in TE cells. In the images, some fluorescence can be seen, but that is for particles outside the cells. It was also observed that CS-F control particles were not internalized by the cancer cells, thereby demonstrating folate receptor mediated specific targeting. Some fluorescence appeared within the cell, but it was significantly weak as compared to targeted particles (CS-A to CS-E). From the images, it is evident that HNPs show more uptake than CS NPs and non cross-linked HNPs show more uptake than cross-linked HNPs.

While various embodiments of the present invention have been shown and described herein, it will be obvious that such embodiments are provided by way of example only. Numerous variations, changes and substitutions may be made without departing from the invention herein. Accordingly, it is intended that the invention be limited only by the spirit and scope of the appended claims.

References (the entirety of each of which is incorporated by reference herein):
1. S. S. Davis, L. Illum and S. Stolnik, *Current Opinion in Colloid & Interface Science*, 1996, 1, 660-666.
2. H. Honarkar and M. Barikani, *Monatshefte Fur Chemie*, 2009, 140, 1403-1420.
3. R. Jayakumar, K. P. Chemazhi, R. A. A. Muzzarelli, H. Tamura, S. V. Nair and N. Selvamurugan, *Carbohydrate Polymers*, 2010, 79, 1-8.
4. S. A. Agnihotri, N. N. Mallikarjuna and T. M. Aminabhavi, *Journal of Controlled Release*, 2004, 100, 5-28.
5. T. Nam, S. Park, S.-Y. Lee, K. Park, K. Choi, I. C. Song, M. H. Han, J. J. Leary, S. A. Yuk, I. C. Kwon, K. Kim and S. Y. Jeong, *Bioconjugate Chemistry*, 2010, 21, 578-582.
6. Q. L. Nie, W. B. Tan and Y. Zhang, *Nanotechnology*, 2006, 17, 140-144.
7. M. Sandros, M. Behrendt, D. Maysinger and M. Tabrizian, *Advanced Functional Materials*, 2007, 17, 3724-3730.
8. G. Skjåk-Bræk, T. Anthonsen and P. Sanford, Editors, eds., *Chitin and Chitosan. Sources, Chemistty, Biochemistry, Physical Properties and Applications*, Elsevier Applied Science Publishers, London 1989.
9. W. K. Wan, L. Yang and D. T. Padavan, *Nanomedicine*, 2007, 2, 483-509.
10. K. D. Yao, T. Peng, Y. J. Yin, M. X. Xu and M. F. A. Goosen, *Journal of Macromolecular Science-Reviews in Macromolecular Chemistry and Physics*, 1995, C35, 155-180.
11. V. Dodane and V. D. Vilivalam, *Pharmaceutical Science & Technology Today*, 1998, 1, 246-253.
12. L. Ilium, *Pharmaceutical Research*, 1998, 15, 1326-1331.
13. B. Wilson, M. K. Samanta, K. Santhi, K. P. S. Kumar, M. Ramasamy and B. Suresh, *Nanomedicine: Nanotechnology, Biology and Medicine*, 2010, 6, 144-152.
14. Y. Sakurai, T. Okano, K. Kataoka, N. Yamada, S. Inoue and M. Yokoyama, 1997.
15. A. Richard and A. Margaritis, *Critical Reviews in Biotechnology*, 2001, 21, 219-232.
16. D. Sgouras and R. Duncan, *STP Pharma Sci.*, 1994, 4, 87-94.
17.1. Hajdu, M. Bodnár, G. Filipcsei, J. Hartmann, L. Daróczi, M. Zrínyi and J. Borbély, *Colloid & Polymer Science*, 2008, 286, 343-350.
18. Y.-H. Lin, C.-K. Chung, C.-T. Chen, H.-F. Liang, S.-C. Chen and H.-W. Sung, *Biomacromolecules*, 2005, 6, 1104-1112.
19. S.-F. Peng, M.-J. Yang, C.-J. Su, H.-L. Chen, P.-W. Lee, M.-C. Wei and H.-W. Sung, *Biomaterials*, 2009, 30, 1797-1808.
20. Z. Keresztessy, M. Bodnar, E. Ber, I. Hajdu, M. Zhang, J. Hartmann, T. Minko and J. Borbély, *Colloid & Polymer Science*, 2009, 287, 759-765.
21. S. Santra, P. Zhang, K. Wang, R. Tapec and W. Tan, *Analytical Chemistry*, 2001, 73, 4988-4993.
22. P. Tanury, S. Kar, S. Bamrungsap, Y. F. Huang, W. H. Tand and S. Santra, *Chemical Communications*, 2009, 2347-2349.
23. M. Huang, E. Khor and L.-Y. Lim, *Pharmaceutical Research*, 2004, 21, 344-353.
24. L. Kong, Y. Gao, G. Lu, Y. Gong, N. Zhao and X. Zhang, *European Polymer Journal*, 2006, 42, 3171-3179.
25. V. I. Pedroni, P. C. Schulz, M. E. Gschaider and N. Andreucetti, *Colloid & Polymer Science*, 2003, 282, 100-102.
26. M. Bodnar, J. F. Hartmann and J. Borbely, *Biomacromolecules*, 2005, 6, 2521-2527.
27. R. J. N. Hjerde, K. M. Vårum, H. Grasdalen, S. Tokura and O, Smidsrød, *Carbohydrate Polymers*, 1997, 34, 131-139.
28. K. M. Vårum, M. M. Myhr, R. J. N. Hjerde and O, Smidsrod, *Carbohydrate Research*, 1997, 299, 99-101.
29. K. Tomihata and Y. Ikada, *Biomaterials*, 1997, 18, 567-575.

---

---

The invention claimed is:

1. A stabilized chitosan-based nanoparticle comprising:
a chitosan polymer and a polyglutamic acid; wherein chains of the chitosan polymer electrostatically interact with chains of the the polyglutamic acid to form an entangled network comprising the chitosan polymer and the polyglutamic acid; and
wherein the polyglutamic acid and the chitosan polymer are at a molar ratio of from 1:5 to 1:20 polyglutamic acid to chitosan polymer and the polyglutamic acid is of a molecular weight such that the nanoparticle has a particle size of between about 20 nm and about 100 nm and has a zeta potential of at least +32 mV.

2. The stabilized chitosan-based nanoparticle of claim 1, wherein the nanoparticle comprises a transmittance value of at least 99% at 500 nm and at a pH of about 7.4 or less.

3. The stabilized chitosan-based nanoparticle of claim 1, further comprising an imaging agent linked to the nanoparticle, wherein the imaging agent comprises at least one of a fluorophore and a paramagnetic chelate having a paramagnetic ion bound therein such that the nanoparticle is effective as an MRI contrast medium.

4. The stabilized chitosan-based nanoparticle of claim 1, further comprising a target-specific ligand linked to the nanoparticle, wherein the target-specific ligand has a binding affinity for a predetermined molecular target.

5. The stabilized chitosan-based nanoparticle of claim 4, wherein the ligand is selected from the group consisting of an aptamer, a peptide, an oligonucleotide, folate, an antigen, an antibody, and combinations thereof.

6. The stabilized chitosan-based nanoparticle of claim 1, wherein the nanoparticle is free from a cross-linking compound that covalently links the chains of the chitosan polymer to the chains of the hydrophilic dispersing agent.

7. The stabilized chitosan-based nanoparticle of claim 1 made by the process comprising reacting components of a first microemulsion and a second microemulsion for a time sufficient to form a stabilized chitosan-based nanoparticle comprising a chitosan polymer and a hydrophilic dispersing agent, wherein the first microemulsion comprises an oil, a surfactant, and an aqueous phase comprising a chitosan polymer and the second microemulsion comprises an oil, a surfactant, and an aqueous phase comprising a hydrophilic dispersing agent; and recovering the stabilized chitosan-based nanoparticle from the reacted first and second microemulsion components.

8. The stabilized chitosan-based nanoparticle of claim 7, wherein a molar ratio of the hydrophilic dispersing agent to the chitosan polymer is about 1:10.

9. The stabilized chitosan-based nanoparticle of claim 1, wherein the molar ratio is about 1:10.

* * * * *